United States Patent
Liu et al.

(10) Patent No.: US 11,702,764 B2
(45) Date of Patent: Jul. 18, 2023

(54) VISUAL CONTINUOUS SPATIAL DIRECTED EVOLUTION METHOD

(71) Applicant: SHENZHEN INSTITUTES OF ADVANCED TECHNOLOGY, Shenzhen (CN)

(72) Inventors: Chenli Liu, Shenzhen (CN); Wangsheng Lai, Shenzhen (CN); Qian Chen, Shenzhen (CN); Ting Wei, Shenzhen (CN); Chenjian Sun, Shenzhen (CN)

(73) Assignee: Shenzhen Institutes of Advanced Technology, Shenzhen (CN)

(*) Notice: Subject to any disclaimer, the term of this patent is extended or adjusted under 35 U.S.C. 154(b) by 92 days.

(21) Appl. No.: 16/904,549

(22) Filed: Jun. 17, 2020

(65) Prior Publication Data
US 2020/0332282 A1    Oct. 22, 2020

Related U.S. Application Data

(63) Continuation of application No. PCT/CN2017/120164, filed on Dec. 29, 2017.

(30) Foreign Application Priority Data

Dec. 27, 2017 (CN) .......................... 201711446362.3

(51) Int. Cl.
*C40B 30/06* (2006.01)
*C12N 7/00* (2006.01)
(Continued)

(52) U.S. Cl.
CPC ............... *C40B 30/06* (2013.01); *C12N 7/00* (2013.01); *C12N 15/1058* (2013.01);
(Continued)

(58) Field of Classification Search
None
See application file for complete search history.

(56) References Cited

FOREIGN PATENT DOCUMENTS

| CN | 107418964 A | 12/2017 |
|---|---|---|
| WO | 2012086381 A2 | 6/2012 |

OTHER PUBLICATIONS

Esvelt et al. (2011) Nature vol. 472 pp. 499 to 503 and supplemental materials pp. 1 to 2.*

(Continued)

*Primary Examiner* — Christian C Boesen
(74) *Attorney, Agent, or Firm* — Jenkins, Wilson, Taylor & Hunt, P.A.

(57) ABSTRACT

A visual continuous spatial directed evolution method is disclosed. The host grows and moves in a solid culture space, the host carrying a foreign target gene to be evolved and containing a gene element that assists the evolution of the target gene, the target gene being correlated with the growth and movement of the host. Depending on different spatial distribution patterns formed in the solid culture space during the growth and movement of the host, screening is performed to obtain an evolved product. This method is carried out directly in the solid culture space. Depending on images of different spatial distribution morphologies visible to the naked eye that are locally formed, selection of evolved products is performed without the need for liquid fed-batch culture equipment. In addition, the evolution effect is visually observed through the infection spots formed during evolution, so that no real-time monitoring equipment is required.

18 Claims, 5 Drawing Sheets
Specification includes a Sequence Listing.

(51) Int. Cl.
*C12N 15/10* (2006.01)
*C12N 15/70* (2006.01)
*C12N 15/85* (2006.01)
*C40B 50/06* (2006.01)
*C40B 60/08* (2006.01)

(52) U.S. Cl.
CPC ............ *C12N 15/70* (2013.01); *C12N 15/85* (2013.01); *C40B 50/06* (2013.01); *C40B 60/08* (2013.01)

(56) References Cited

OTHER PUBLICATIONS

Jin et al. (2011) International Journal of Molecular Sciences vol. 12 pages 3055 to 3071.*
International Search Report issued in corresponding International application No. PCT/CN2017/120164, dated Oct. 8, 2018(11 pages).
First Office Action from China patent office in a counterpart Chinese patent Application 201711446362.3, dated May 11, 2020 (10 pages).
Journal of Anhui Agri. Sci. 2011.39(3),1310-1314(6 pages).
Carlson et al. (2014) "Negative Selection and Stringency Modulation in Phage-Assisted Continuous Evolution," Nature Chemical Biology, vol. 10, No. 3, pp. 216-222.
Communication pursuant to Rules 70(2) and 70a(2) EPC corresponding to European Patent Application No. 17936940.0-1118 dated Sep. 28, 2021.
Dickinson et al. (2014) "A system for the continuous directed evolution of proteases rapidly reveals drug-resistance mutations," Nature Communications, vol. 5, No. 1, 8 pages.
Extended European Search Report corresponding to European Patent Application No. 17936940.0-1118 dated Sep. 10, 2021.
Ranjbariyan et al., "Molecular identification of antagonistic bacteria from Tehran soils and evaluation of their inhibitory activities toward pathogenic fungi," Iranian Journal of Microbiology, vol. 3, No. 3, pp. 140-146 (2011).
Xiao et al. (2015) "Synthetic Biology in Studying the Origin of Life, Evolution, and Structure-Function Relation," Scientia Sinica Vitae, vol. 45, No. 10, pp. 915-927 (English Abstract).

* cited by examiner

VISUAL CONTINUOUS SPATIAL DIRECTED EVOLUTION METHOD

CROSS-REFERENCE TO RELATED APPLICATIONS

This application is a continuation of co-pending International Patent Application No. PCT/CN2017/120164 filed on Dec. 29, 2017 which claims the priority and benefit of Chinese patent application number 201711446362.3, entitled "Visual Continuous Spatial Directed Evolution Method" and filed Dec. 27, 2017 with China National Intellectual Property Administration, the entire contents of which are incorporated herein by reference.

TECHNICAL FIELD

This disclosure relates to the field of directed evolution and screening, and more particularly relates to a visual continuous spatial directed evolution method.

BACKGROUND

Directed evolution, also called laboratory evolution, is a powerful technical method that can produce biological molecules having specified functions by steering the biological evolution process. The biomolecules such produced have been widely used in many fields such as industrial production, bioengineering, and pharmaceutical development. The Harvard David R Liu laboratory developed a continuous evolution system based on phage growth (phage-assisted continuous evolution, PACE). PACE is mainly composed of three modules: LWS, CCP, and IMP. LWS (Leading Phage Waiting for Selection) represents a phage module, in which the gene III (gIII) in the genes of the M13 bacteriophage that is required for packaging and infecting the host bacteria is excised, and is replaced with the gene of a biomolecule to be evolved. After removal of the gIII, the bacteriophage is unable to infect the host to produce progeny phages. IMP (Inducible Mutagenesis Plasmid) stands for a mutagenesis module, which uses arabinose as an inducer to induce the expression of DNAQ926, dam, and seqA, so that the erroneous bases introduced by the polymerase during DNA replication cannot be excised, thereby increasing the mutation rate. The IMP inducible by arabinose may increase the phage mutation rate by hundreds of folds. CCP (Complementary Component Plasmid) refers to an accessory module, which contains the gIII required by the phage to infect the host cell and reproduce. Thus, the expression of gIII on CCP is linked to the biological activity of the target gene to be evolved on LWS (e.g., to have an RNA polymerase evolve in a specific direction, a promoter consistent with the direction of evolution may be used to control the expression of gIII), so that it can be determined whether each mutant LWS is able to produce progeny bacteriophages LWS having infectious activity.

In the evolution pool, when the phage carrying the wild-type target gene to be evolved infects the host cell, the phage injects its genetic material namely the wild-type LWS into the host bacterium, and uses the replication system within the host bacterium to replicate its own genetic material. At the same time, under the induction of arabinose, the DNAQ926, dam, and seqA on the IMP in the host cell are expressed, leading to mutations on LWS. If a mutation acquired by LWS (i.e., a mutation of the target gene on LWS) can turn on the expression of gIII, then infectious progeny phages may be produced. These newly generated progeny phage mutants LWSe are secreted out of the host bacterium to infect a new host bacterium for the next round of proliferation. As a result, those LWSe mutants that can turn on gIII expression can continue to multiply and increase their numbers, while the wild-type LWS and those LWS mutants that cannot activate gIII expression will not be able to secrete infectious progeny phages for proliferation, and so their numbers will not increase. At this time, if new host bacterial culture medium is continuously added to the evolution pool and the old culture medium is continuously discharged at a certain flow rate, then the wild-type LWS and its mutants that cannot turn on gIII expression or have a low expression capacity will soon be eluted, while those LWSe mutants that are able to efficiently activate gIII expression will eventually be retained.

Such a system however is bulky and requires a complete set of automatic fed-batch culture equipment with a high-sensitivity real-time monitoring system for continuous fed-batch culture. Different evolved products are mixed and diluted together in the whole culture tank, making it difficult for direct detection and separation of these products. The system also requires a large consumption of reagent, the culture equipment incurs a relatively high cost, and the evolution operations are complicated. Furthermore, the system can only evolve one target gene at a time, hence a low throughput.

In view of this, the present disclosure is proposed.

SUMMARY

In order to solve the problems of difficulty in detection and separation of samples, low throughput, high cost, and complicated evolution operations in existing methods, the present disclosure provides a visual continuous spatial directed evolution method, which is directly carried out on the surface of a solid culture space, such as a solid culture plate, without the need for liquid fed-batch culture equipment. Furthermore, the evolution effect can be visually observed through the spatial morphology and distribution of the infection spots formed during evolution. Thus, no real-time monitoring equipment is required, the operations are simple and the throughput is high, and multiple sets of evolution experiments can be performed at a time.

To achieve the above object of the present disclosure, the following technical solutions are adopted.

There is provided a visual continuous spatial directed evolution method, in which a host grows and moves in a solid culture space, the host carrying a foreign target gene to be evolved, the host itself containing a genetic element that assists the evolution of the target gene, the target gene being correlated with the growth and movement of the host.

Depending on different spatial distribution patterns formed in the solid culture space during the process of growth and movement of the host, screening is performed to obtain an evolved product.

In the visual continuous spatial directed evolution method (Spatial Phage-Assisted Continuous Evolution, SPACE), the system contains the target gene to be evolved and the host. The host contains a genetic element that assists the evolution of the target gene, and the target gene is correlated with the host. The target gene evolves along with the growth and movement of the host in the solid culture space. After evolution, different spatial distribution patterns visible to the naked eye are formed, and the evolved products may be selected depending on this state.

The entire evolution and screening process stretches out on the two-dimensional plane or in the three-dimensional space, and different evolved products are distributed in different areas of the plane and will not be mixed with each other. Depending on the difference of their activities, each product locally forms an image of a different spatial distribution pattern visible to the naked eye. As the evolution continues, this image will continuously be enlarged. Once an evolved product appears, an image may be directly formed at the corresponding position. Even if the product exists in a very small amount, this image will not be diluted or obscured. Thus, depending on the state of the image, the evolved product that meets the desired needs may be directly selected out and separated. The system is easy to operate, has low cost, and does not require special equipment, and a single person can perform multiple sets of evolution experiments at a time, making it possible to conduct directed evolution of a target gene with high throughput.

Further, the target gene may be located in the genome or a plasmid of the host or in a parasite corresponding to the host. The target gene may be inserted into the host genome by gene recombination, or the target gene may be transferred to a plasmid in the host or the parasite may be used to invade the host, thus realizing the purpose of the host containing the target gene to be evolved.

Further, the parasite may include any one selected from the group consisting of a bacteriophage, a cyanophage, an animal or plant virus, a fungal virus, a mycoplasma, a chlamydia, and a bacterium.

Further, the parasite may be a bacteriophage.

The host is any one of the following:

a non-defective strain of a natural host bacterium of the bacteriophage;

a bacterial strain obtained by genetic modification of a non-defective strain of a natural host bacterium of the bacteriophage;

a non-natural host bacterium that only acquires its susceptibility after being genetically modified.

Further, the host may include *Escherichia coli, Pasteurella, Shigella, Pseudomonas, Xanthomonas, Salmonella, Staphylococcus aureus*, and modified strains obtained by genetic modification to change their susceptibility.

Exemplarily, the host may be *Escherichia coli* carrying F factor (fertility factor).

Further, the bacteriophage may be a temperate bacteriophage, a virulent bacteriophage, or a chronic infectious bacteriophage.

Further, the bacteriophage may include a filamentous bacteriophage, T4 bacteriophage, T7 bacteriophage, λ bacteriophage, P1 bacteriophage, P2 bacteriophage, P22 phage, φX174 bacteriophage, and SP6 bacteriophage.

Exemplarily, the filamentous bacteriophage may include M13 filamentous bacteriophage and f1 filamentous bacteriophage.

As an exemplary solution of the present disclosure, the bacteriophage is M13 bacteriophage, in which the gIII required for packaging and infecting the host bacteria is excised, and correspondingly, the gene element such as a helper plasmid that assists the evolution of the gene of interest contains the above-mentioned gIII. The bacteriophage is able to normally invade the host bacteria and perform DNA replication. But in the absence of the related helper plasmid, progeny with infectious activity cannot be packaged.

Further, the target gene may be a combination of coding sequences and/or non-coding sequences, the coding sequences coding for one or more proteins.

Further, the target gene may include one or more selected from the group consisting of T7 RNA polymerase gene, a protease gene, a cellulase gene, a fluorescent protein gene, and a quorum-sensing gene.

Further, the gene element that assists the evolution of the target gene may be a mutagenesis plasmid, and the expression of the mutagenesis plasmid may be activated or induced by the target gene before and after evolution separately.

Exemplarily, the mutagenesis plasmid may contain a mutagenic gene including at least one selected from the group consisting of a DNAQ gene mutant—DNAQ926 gene—in which the 12- and 14-position amino acids are each mutated to Ala, deoxyadenosine methylase dam gene, hemimethylated GATC binding protein seqA gene, activation-induced cytidine deaminase gene AID, uracil DNA glycosylase inhibitor gene Ugi in phage PBS2, and transcription repressor emrR.

Mutagenic genes may increase the mutation rate of genetic information during transferring processes such as replication and transcription. Mutagenesis plasmids IMPs may be induced and expressed by the same method (e.g., a psp promoter may be used for induction control). In different embodiments, if there are multiple mutagenesis plasmids IMPs such as IMP1, IMP2, IMP3, etc., then these mutagenesis plasmids may be the same as one another. Alternatively, the expression of the mutagenesis plasmids IMPs may also be directly activated by the target genes before and after evolution separately, then in this case IMP1 and IMP2 represent different IMPs.

Further, the solid culture space may include a two-dimensional planar culture structure and a three-dimensional space culture structure.

Further, the continuity of the movement and evolution in the vertical direction in the solid culture space is maintained by regularly forming a cast solid culture system.

Further, the directed evolution is a high-throughput evolution.

Further, the high-throughput evolution may be achieved by using multiple sets of solid culture spaces or by using different positions in the solid culture space.

Further, the target gene may be correlated with the growth and movement of the host through a helper plasmid. The helper plasmid may contain at least a first helper plasmid, the first helper plasmid being a helper plasmid CCP1 or a helper plasmid CCP2, where the nucleic acid sequence of the helper plasmid CCP1 is shown in SEQ ID NO: 3, and the nucleic acid sequence of the helper plasmid CCP2 is shown in SEQ ID NO: 4.

The helper plasmid CCP1 or helper plasmid CCP2 supports low-level proliferation of the phage before evolution, and the target gene having increased activity after evolution enables the helper plasmid CCP1 or helper plasmid CCP2 to support the phage to be evolved to a higher level of proliferation.

Further, the helper plasmid may include a second helper plasmid, the second helper plasmid being a helper plasmid CCP3 or a helper plasmid CCP4, where the nucleic acid sequence of the helper plasmid CCP3 is shown in SEQ ID NO: 5.

The helper plasmid CCP3 and helper plasmid CCP4 have functional defects causing them unable to support the proliferation of the phage before evolution.

In particular, a host bacterium S1 carrying IMP1 and CCP1 grows and moves on the culture plate. The host bacterium S1 comes into contact with the bacteriophage LWS during movement, and carries the LWS allowing the LWS to evolve until the bacteriophage LWSe carrying the evolved target gene is produced. The bacteriophage LWS has defects in proliferation. Pre-evolution LWS uses the background expression of CCP1 to carry out low-level infection and proliferation. The function of the evolved target gene is at least partially linked to the function of the gene element on CCP2 that supports the proliferation of the post-evolution phage LWSe. Therefore, LWSe may use CCP1 to perform efficient infection and replication in S1. Efficient infection and replication of the phages may inhibit the growth of host bacteria, resulting in a clear infection spot visible to the naked eye that contains fewer bacteria formed in the LWSe infected area. Depending on this infection spot, the evolution effect can be directly analyzed.

Further, the host bacterium may include host bacterium S2 or host bacterium S3 which grows and moves on the culture plate. The host bacterium S2 comes into contact with the initially evolved phage LWSe during movement, and carries the LWSe allowing the LWSe to evolve until the phage LWSeN carrying the further evolved target gene is produced. The host bacterium S2 may contain the helper plasmid CCP2 that supports the proliferation of post-evolution phage LWSe or LWSeN, the helper plasmid CCP3 that inhibits the proliferation of pre-evolution phage LWS, and a mutagenesis plasmid IMP2. The function of the evolved target gene is at least partially linked to the function of the gene element on CCP2 that supports the proliferation of the post-evolution phage LWSe or LWSeN. The function of the gene elements on CCP3 and CCP4 is linked to the function of the target gene before evolution. Meanwhile, the gene elements carried by CCP3 and CCP4 have functional defects and cannot support the proliferation of pre-evolution phage LWS. This operation may reduce the wild-type activity of the target gene on the bacteriophage LWSeN. Thus, when the wild-type activity of the target gene in the bacteriophage LWSeN is reduced to a sufficiently low level, the LWSeN may be able to use CCP2 to perform efficient infection and replication in S2. Efficient infection and replication of the phages may inhibit the growth of host bacteria, resulting in a clear infection spot visible to the naked eye that contains fewer bacteria formed in the bacteriophage LWSeN infected area. Depending on this infection spot, the evolution effect can be directly analyzed. The host bacterium S3 may contain the helper plasmid CCP2 that supports the proliferation of post-evolution phage LWSe or LWSeN, the helper plasmid CCP4 that inhibits the proliferation of pre-evolution phage LWS, and the mutagenesis plasmid IMP2. CCP4 is a high-copy plasmid with even higher levels of expression of defective gene elements. Thus, CCP4 is an enhanced version of CCP3. The S3 bacterium is used to replace S2 bacterium for further evolving the bacteriophage LWSe. Similarly, the CCP2 plasmid has a lower copy number than that of CCP1. The low-copy CCP2 has a relatively low level of background expression, and so cannot support the proliferation of pre-evolution phage LWS, thus providing a stronger evolutionary selection pressure.

Further, the method may include the operation in which when the host bacteria move to the edge of the plate, the host bacteria and the post-evolution phages are transferred to the next plate for continued evolution.

Further, the directed evolution may be carried out by using different hosts in succession, and the gene element contained in the latter host that supports phage proliferation includes a helper plasmid that supports the proliferation of the post-evolution phages, and a helper plasmid that inhibits the proliferation of the pre-evolution phage.

Compared with the related art, the present disclosure may offer the following beneficial effects.

(1) The visual continuous spatial directed evolution method provided by the present disclosure is endowed with a spatial attribute. The entire evolution process is carried out on a two-dimensional planar space or in a three-dimensional space, where the space serves the dual purpose of a supporting platform and an evolutionary selection pressure. As long as a small amount of an evolved product appears, a spatial distribution pattern such as a plaque may be formed directly at the corresponding position. Thus, based on the size of the infection spots, the counts of plaques formed during evolution, or the real-time monitoring of a reporter gene, the activity of the target gene and the proliferation activity of the bacteriophages may be shown, and further the evolved product may be directly identified and separated without the need for liquid fed-batch culture equipment or real-time monitoring equipment.

(2) According to the visual continuous spatial directed evolution method provided by the present disclosure, the evolution results appearing in different spatial positions will be fixed at their respective positions, and will not be washed out and mixed by other components, and so can be directly separated. The signal of each of the evolution results appearing in different spatial positions will be amplified along the direction of evolution, and the evolution effect will be enhanced, thus providing higher detection sensitivity.

(3) The visual continuous spatial directed evolution method provided by the present disclosure offers simple evolution operations and high throughput, so that multiple sets of evolution experiments may be performed at a time.

BRIEF DESCRIPTION OF DRAWINGS

For a better understanding of the technical solutions reflected in embodiments according to the present disclosure or those technical solutions used in the related art, the drawings required for the description of these embodiments of the related art will be briefly described below.

DETAILED DESCRIPTION

Hereinafter implementation solutions in accordance with the present disclosure will be described in detail in connection with illustrative embodiments, but those skilled in the art will appreciate that the following embodiments are intended for the mere purpose of illustrating the present disclosure and are not to be construed as limiting the scope of the present disclosure. Where no specific conditions are indicated in the embodiments, the conventional conditions or the conditions recommended by the manufacturer shall be followed. Reagents or instruments as used herein, for which no manufacturer is indicated, are all conventional products that are commercially available.

In the visual continuous spatial directed evolution method provided by the present disclosure, when the phages and the host bacteria are mixed and coated on a plate, due to the growth difference between the host bacteria infected with the M13 phage and the uninfected host bacteria, plaques visible to the naked eye will be formed. Considering that the reporter gene has problems in terms of specificity, sensitivity, and operability, the present disclosure does not use the reporter gene, but directly uses the plaques formed during the infection process as an indicator signal for SPACE, thereby visualizing SPACE.

Figure 1:
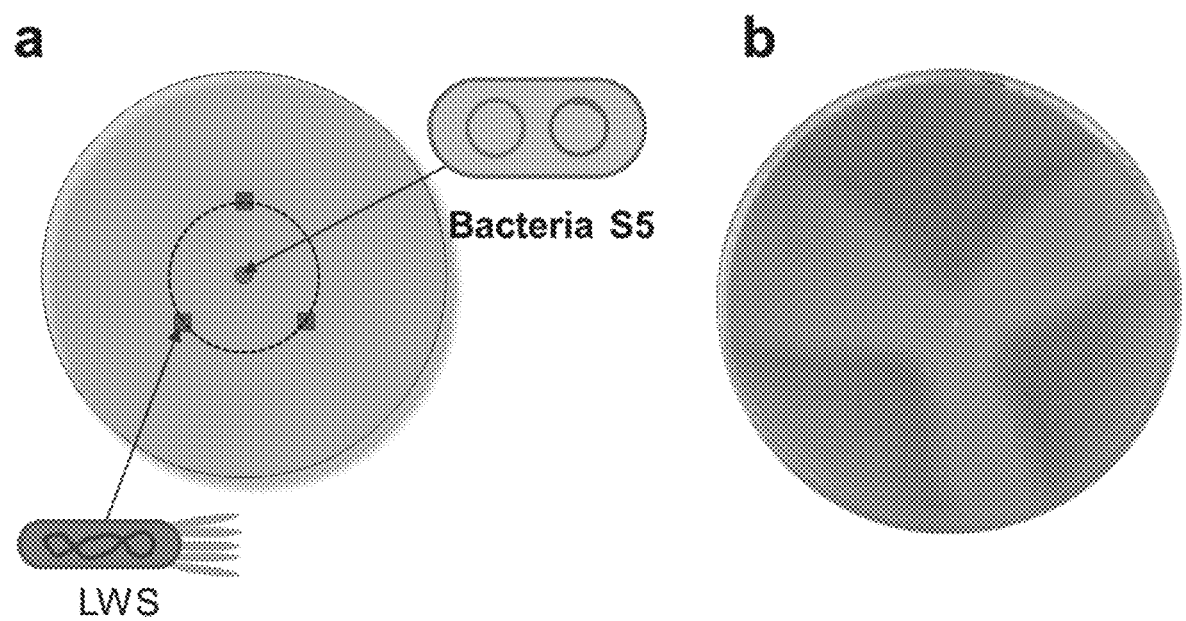
FIG. 1 is a schematic diagram illustrating the effects of the movement of host bacteria and the infection spots in accordance with an embodiment of the present disclosure.

As in the plaque formation experiment, the host bacteria are inoculated in the center of a culture plate, and wild bacteriophages are inoculated on each of three corners of a triangle that surround the host bacteria (Sub-figure a of FIG. 1). Thus, the host bacteria grow on the plate while moving toward the edge of the plate. The host bacteria in motion then come into contact with the phages and are infected by the phages to produce progeny phages, while continuing moving towards the outer edge. Because infected host bacteria grow slower while the host bacteria in the uninfected area maintain their original state, A V-shaped infection spot containing fewer bacteria may be seen in the infected area (Sub-figure b of FIG. 1). The presence of this clear infection spot could be used to indicate the presence of phage infection, and the degree of transparency and size of the clear infection spot may represent the infectious activity of the phages.

Figure 2:
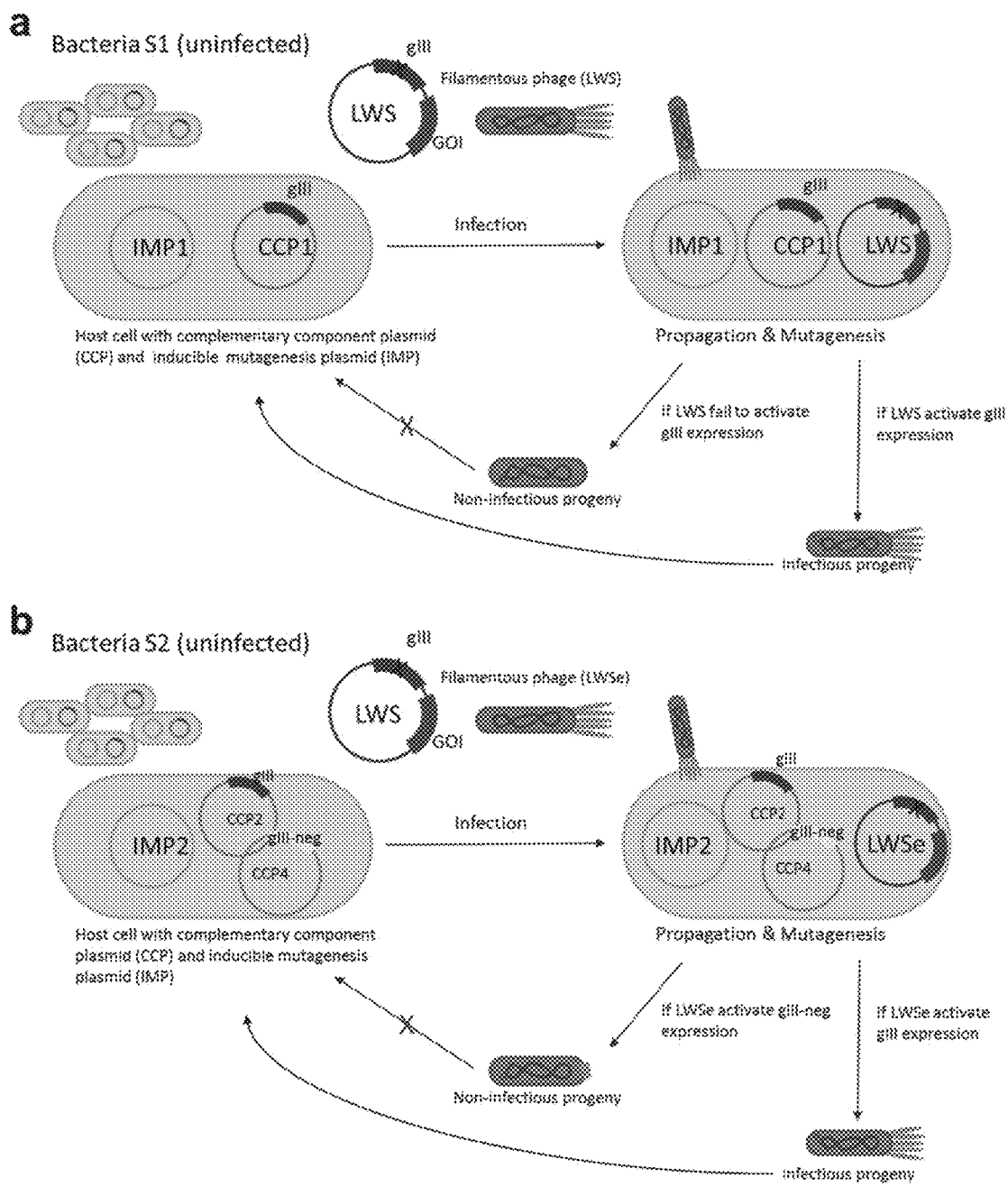
FIG. 2 is a schematic diagram illustrating the principle of continuous spatial directed evolution in accordance with an embodiment of the present disclosure.
Figure 3:
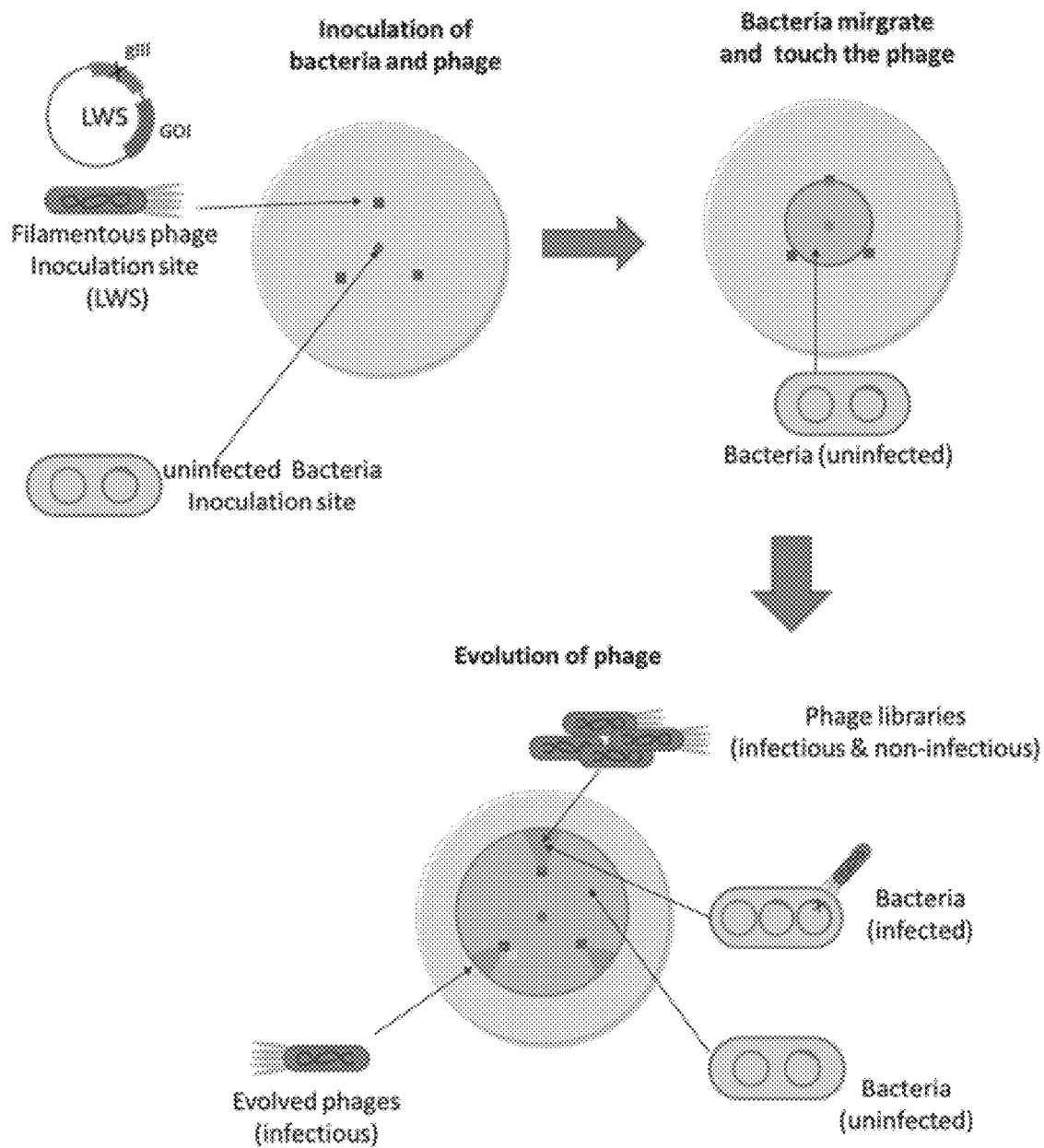
FIG. 3 is a schematic diagram illustrating a continuous spatial directed evolution model in accordance with an embodiment of the present disclosure.
Figure 4:
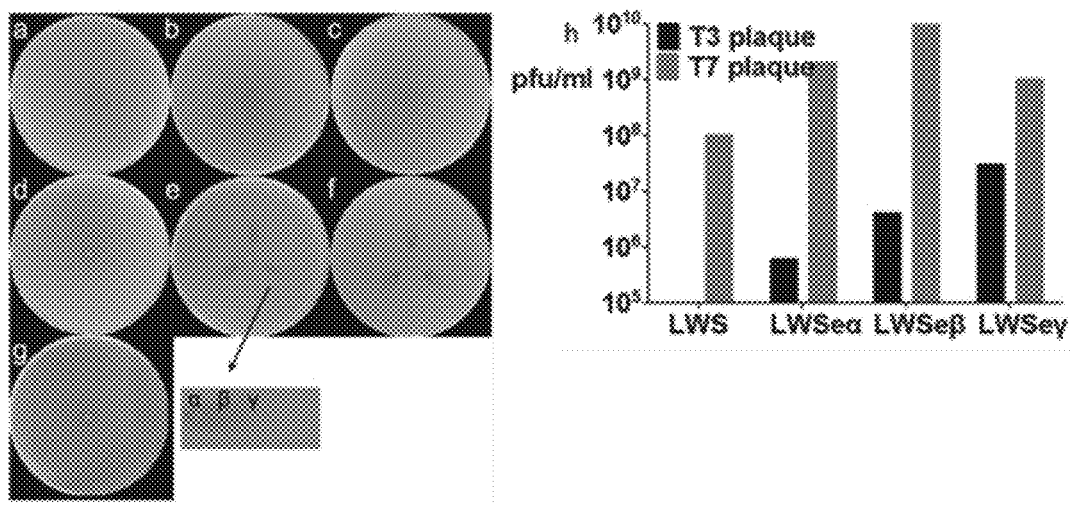
FIG. 4 is a diagram illustrating the evolution results of a first round of SPACE positive screening in accordance with Embodiment 4 of the present disclosure.

Inspired by the inventors' early study of spatial evolution systems, the core design principles of SPACE are illustrated in FIGS. 2 and 3. In particular, when the phage LWS carrying the gene of interest infects the host bacterium containing the mutagenesis plasmid IMP and the helper plasmid CCP, the phage genome replicates and mutates. If a mutant progeny LWS is able to activate the expression of gIII on CCP, then progeny bacteriophages LWSe having infectious activity will be produced and the next round of infection and evolution will begin. Otherwise, defective progeny phages having no infectious activity will be produced. As evolution progresses, LWSe will continue to increase, while wild-type LWS bacteriophages and progeny bacteriophages having defects in infectious activity will not increase or may increase in very little amounts. As illustrated in the figure, the GOI (gene of interest) on the LWS represents the target gene to be evolved.

The host bacteria containing CCP and IMP are inoculated in the center of the culture plate, and the bacteriophages LWS are inoculated on each of three corners of a triangle that surround the host bacteria. Then the host bacteria undergo growth and division on the plate, and at the same time uses their own flagella to move to the edge of the plate, and at a specific position come into contact with the phages LWS which are inoculated there in advance. The bacteriophage LWS invades the host bacterium and is carried by the host bacterium to move forward. At the beginning, the bacteriophages LWS are not able to turn on the expression of gIII on CCP, and could only use the background expression of CCP for low-level proliferation. At this time, the phage proliferation level is very low, and so has a relatively small impact on the host bacteria. As such, the infected host bacteria and the uninfected host bacteria grow and divide at almost the same rate, and no difference can be seen in their morphologies. At the same time, because the low-level proliferation rate of the bacteriophages LWS cannot match the growth and movement speed of the host bacteria, these inefficient bacteriophages LWS will soon be left behind by the moving host bacteria.

While the bacteriophages LWS are proliferating, they also use IMP for mutation and evolution until the bacteriophage LWSe that is able to effectively activate the expression of CCP is evolved. At this point, the bacteriophage LWSe directly activates the gIII on CCP, allowing itself to efficiently proliferate and continuously produce progeny bacteriophages, which continue to infect the bacteria in movement. The efficient proliferation of the bacteriophage LWSe will disrupt the growth of the host bacteria, causing the bacteria to grow slower. Thus, after the bacteriophage LWSe is evolved, a clear area where the host bacteria grow slower and where there are fewer bacteria may appear at the corresponding position. As the evolution progresses and the bacteria infected by the bacteriophage LWSe continue to move, this clear area will continue to expand along the direction of movement, and eventually form a V-shaped infection spot on the plate that is visible to the naked eye. The closer to the outside of the infection spot, the longer the evolution time, and the more obvious the evolution effect. We thus may obtain the desired post-evolution phage LWSe directly in the infection spot.

As illustrated in FIGS. 2 and 3, the phage-assisted continuous spatial directed evolution system in accordance with an embodiment of the present disclosure may include two parts: a positive screening (a) part and a negative screening (b) part. Note, from the perspective of implementation of the present disclosure, only the positive screening (a) part is needed to achieve the purpose of evolving the target gene to be evolved into the evolved target gene. Thus, the negative screening (b) part may be regarded as a further improved technical solution of the directed evolution system of the present disclosure. In fact, the positive screening (a) part realizes a qualitative change from "target gene to be evolved" to "evolved target gene", while the negative screening (b) part realizes a quantitative change in which the function of the "evolved target gene" is further enhanced.

As used herein, the term "target gene to be evolved" (gene of interest, GOI) is used interchangeably with "target gene before evolution", namely the target gene that has not undergone evolutionary mutation through the system and method in accordance with the present disclosure, and in some cases may be called "wild-type gene". The term "evolved target gene" is relative to the "target gene to be evolved", and it has a new function that is evolved. However, the "evolved target gene" may also have the original function. Of course, the original function may completely disappear. In short, in this disclosure, as long as the target gene has an evolved new function, it may be called an "evolved target gene", regardless of whether the original function still exists.

In addition, terms "phage" and "bacteriophage" are used interchangeably. Terms "gene of interest" and "target gene" are used interchangeably. A "phage before evolution" may also be referred to as a "pre-evolution phage", and a "phage after evolution" may be referred to as a "post-evolution phage" or an "evolved phage". A "target gene before evolution" may be referred to as "a pre-evolution target gene", and a "target gene after evolution" may also be called a "post-evolution target gene" or an "evolved target gene". Furthermore, terms "infection spot" and "plaque" are used interchangeably herein.

It is noted that the symbols as used herein, e.g., LWS, CCP, IMP, and S, are merely exemplary symbols. The objects represented by these symbols may be replaced with other expressions. For example, the bacteriophage LWS may be referred to as a pre-evolution bacteriophage. The bacteriophage LWSe may be called a post-evolution bacteriophage or an evolved phage, and may also be used as a collective term for all evolved phages. The bacteriophage LWSeN may be called a further evolved phage, where the number N (e.g., 1, 2, 3, or other combinations of letters and numbers, etc.) indicates the number of generations of subculturing or the number of evolution times, or may indicate evolution under different conditions. The host bacterium S1 may be referred to as a first host bacterium. The host bacterium S2 may be called a second host bacterium. The host bacterium S3 may be referred to as a third host bacterium. The helper plasmid CCP1 may be called a first helper plasmid. The helper plasmid CCP2 may be called a second helper plasmid. The helper plasmid CCP3 may be called a third helper plasmid. The helper plasmid CCP4 may be called a fourth helper plasmid. The mutagenesis plasmid IMP1 may be called a first mutagenesis plasmid. The mutagenesis plasmid IMP2 may be called a second mutagenesis plasmid. The mutagenesis plasmid IMP3 may be called a third mutagenesis plasmid. The plasmids CCP1 and CCP2 that support the proliferation of the evolved bacteriophage LWSe are also collectively called positive screening CCPs. Similarly, the plasmids CCP3 and CCP4 that inhibit the proliferation of pre-evolution phage LWS are also collectively referred to as negative screening CCPs. The plasmids IMP1, IMP2 and IMP3 used to induce mutations are collectively referred to as IMPs.

In addition, the host bacteria in the present disclosure may include other host bacteria in addition to the above host bacteria S1, S2, and S3. It should also be noted that, as used herein, the host bacteria S1, S2, and S3 do not mean different "bacterial species", but indicate that the helper plasmids or mutagenesis plasmids carried in these strains are different. In this disclosure, the host bacteria S1, S2, and S3 may be obtained by introducing different plasmids into the same bacterial species, such as E. coli carrying F factor.

As illustrated in FIGS. 2 and 3, the phage-assisted continuous spatial directed evolution system according to an embodiment of the present disclosure includes a bacteriophage LWS carrying a gene to be evolved, the phage LWS having proliferation defects. The so-called "proliferation defects" generally refers to defects in some functions that are essential during the bacteriophage's life cycle, such as defects in functions of packaging and/or infecting the host bacteria, which may be caused by mutations in the related genes. In different phages, the genes responsible for packaging and/or infection of host bacteria and other essential functions are different. For example, in one embodiment according to the present disclosure, the bacteriophage LWS is the M13 bacteriophage, in which the gIII required for packaging and infecting the host bacteria is excised, resulting in the inability to normally package and infect the host bacteria. Those skilled in the art will appreciate that any similar bacteriophage may be used as the bacteriophage LWS in the present disclosure, which will not be limited to the M13 bacteriophage.

In the directed evolution system illustrated in FIGS. 2 and 3, the host bacterium S1 contains a helper plasmid CCP1 that supports the proliferation of post-evolution LWSe and a mutagenesis plasmid IMP1. The pre-evolution LWS may use the background expression of CCP1 to carry out low-level infection and proliferation. The support of the helper plasmids CCP1 and CCP2 to the proliferation of post-evolution LWSe is achieved by the function of the evolved target gene being at least partially linked to the function of the gene elements on CCP1 and CCP2 that support the proliferation of post-evolution LWSe. The term "at least partially" means that the function of the evolved target gene may also be partially related to the function of the gene element related to the proliferation of pre-evolution LWS, in addition to the part of the function being linked to the function of the genetic element related to the proliferation of post-evolution LWSe. For example, in one embodiment according to the present disclosure, the pre-evolution target gene refers to the T7 RNA polymerase gene, and the post-evolution or evolved target gene refers to the gene having T3 RNA polymerase function (also including T7 RNA polymerase function). The genetic element on CCP2 refers to the T3 promoter, which controls the expression of the downstream gIII to assist the proliferation of gIII functionally deficient phage LWSe. As such, the T7 RNA polymerase gene is functionally linked with the T7 promoter, and the T3 RNA polymerase gene is functionally linked with the T3 promoter. In addition, in one embodiment according to the present disclosure, IMP1 is activated by T7 RNA polymerase expressed by the target gene carried by the pre-evolution LWS, and induces the mutation and evolution of the LWS. IMP2 is activated by T3 RNA polymerase expressed by the target gene carried by the post-evolution LWSe, and induces LWSe to continue to mutate and evolve.

Those skilled in the art will be able to appreciate that the present disclosure will not be limited to the above-mentioned embodiment using "T7 RNA polymerase gene" as the pre-evolution target gene, but may include any similar technical solutions. In particular, regarding different target genes, such as a protease gene, a cellulase gene, a fluorescent protein gene, a quorum-sensing gene, and an antibody gene, their functions may be linked to the function of the helper plasmid using different principles.

For a better understanding, the following briefly introduces the methods of linking the activity of several other target genes with the gIII on CCP. Note, however, there are many methods of linking the activity of the target gene with gIII, and so they will not be restricted to the following several methods. Regarding the protease gene, a first method is using the degradation sequence of the target protease as a connecting fragment, and fusing the gIII with the gene that codes for an accessory protein (e.g., g6 protein of M13 bacteriophage) operative to bind with and block the gIII protein, for fusion expression. In particular, the degradation sequence mentioned here actually refers to the gene sequence that codes for the protein to be degraded by the target protease. In this case, the gIII part of the expressed fusion protein is blocked and has no activity. Only when the target protease evolves a specific activity and degrades the amino acid sequence expressed by the designated degradation sequence would the gIII having activity be released. A second method is using the T7 polymerase as an intermediary and using the target protease's degradation sequence as a connecting fragment, and subjecting the T7 polymerase and T7 lysozyme to fusion expression thus creating a new polymerase. The activity of this new polymerase is blocked by the T7 lysozyme. Only if the evolved protease is able to recognize the set degradation sequence and excise the lysozyme part, will the resulting polymerase be active.

Regarding the cellulase gene, the lactose operon which is inhibited by the glucose may be used to control the expression of the gIII. Regarding the fluorescent protein gene, a light-inducible promoter sensitive to the fluorescence emitted by the fluorescent protein of interest may be used to activate the expression of the gIII. Regarding the quorum-sensing gene, a quorum-sensing system may be used to control the expression of the gIII. Regarding the antibody gene, the antibody and the transcription factors that control the expression of gIII may be subjected to fusion expression, while the antigenic determinant and the transcriptase are subjected to fusion expression.

The negative screening (b) part in FIG. 2 illustrates a further improved technical solution according to the present disclosure. The system further includes a host bacterium S2 or S3. The host bacterium S2 contains a helper plasmid CCP2 that supports the proliferation of post-evolution LWSe, a mutagenesis plasmid IMP2, and a helper plasmid CCP3. The host bacterium S3 contains the helper plasmid CCP2 that supports the proliferation of post-evolution LWSe, the mutagenesis plasmid IMP2, and a helper plasmid CCP4. The helper plasmid CCP2 and the mutagenesis plasmid IMP2 are similar to those in positive screening (a) part, except that CCP1 is a high-copy plasmid while CCP2 is a low-copy plasmid. IMP1 and IMP2 are activated for expression by the target genes before and after evolution, respectively. However, the function of the genetic elements on CCP3 and CCP4 is linked to the function of the target gene before evolution. Furthermore, CCP3 and CCP4 may have functional defects and so cannot support the proliferation of pre-evolution LWS. In an embodiment according to the present disclosure, the genetic elements on the helper plasmids CCP3 and CCP4 are the T7 promoter, which controls the expression of the gIII-neg gene. The gIII-neg is a defective-type of gIII, which lacks about 70 amino acids between aa280 and aa350 of the pIII (protein expressed by gIII), and so cannot support the proliferation and evolution of LWS. When expressed together with gIII, gIII-neg may competitively inhibit LWS proliferation. Those skilled in the art will appreciate that gIII-neg is also exemplary, and different genes may be used depending on different phages, and different mutations may be taken in the same gene. In addition, in one embodiment according to the present disclosure, IMP2 is activated by the T3 RNA polymerase expressed by the evolved target gene carried by the post-evolution LWSe, and induces the mutation and evolution of the LWSe. In fact, IMP1 and IMP2 may be induced for expression by the same method (e.g., the psp promoter may be used to control the induction), where in this case IMP1 and IMP2 are replaced by the same IMP3 plasmid. The psp promoter is able to sense the infection of the bacterium by the M13 bacteriophage. The psp promoter is usually in a state of self-repression, and the genes under its control are basically not expressed, while when infection occurs the psp promoter would be activated and the genes under its control may be highly expressed. Since the activation of IPM3 for expression is independent of the target gene carried on the phage LWS, the use of IPM3 in place of IPM1 and IPM2 does not require replacement of the IMP plasmids in positive and negative screening. The plasmids IMP1, IMP2, and IMP3 used to induce mutations may be collectively referred to as IMPs.

In an exemplary embodiment according to the present disclosure, the mutagenesis plasmid IMP may contain a mutagenic gene including at least one selected from the group consisting of a DNAQ gene mutant DNAQ926 gene in which the 12- and 14-position amino acids are each mutated to Ala, deoxyadenosine methylase dam gene, hemimethylated GATC binding protein seqA gene, activation-induced cytidine deaminase gene AID, uracil DNA glycosylase inhibitor gene Ugi in phage PBS2, and transcription repressor emrR. They may interfere with the DNA replication process, leading to increased mutation rates. In fact, any gene that is able to increase the mutation efficiency may be used herein as a mutagenic gene.

The directed evolution method provided by the present disclosure includes the following. Host bacterium S1 carrying IMP1 and CCP1 grows and moves on a culture plate. The host bacterium S1 comes into contact with the bacteriophage LWS during the movement, and carries the LWS allowing the LWS to evolve until the bacteriophage LWSe carrying the evolved target gene is produced. The bacteriophage LWS has defects in proliferation. Pre-evolution LWS uses the background expression of CCP1 to carry out low-level infection and proliferation. The function of the evolved target gene is at least partially linked to the function of the gene element on CCP2 that supports the proliferation of LWSe. Therefore, LWSe may use CCP1 to perform efficient infection and proliferation in S1. Efficient infection and proliferation of the phages may inhibit the growth of host bacteria, resulting in a clear infection spot visible to the naked eye that contains fewer bacteria formed in the LWSe infected area. Depending on this infection spot, the evolution effect can be directly analyzed.

As a further improved solution of the above method, the method may further include the following operation in which the host bacterium S2 or S3 separately grows and moves on the culture plate. The host bacterium S2 comes into contact with the initially evolved phage LWSe during the movement, and carries the LWSe allowing the LWSe to continue to evolve until the phage LWSeN carrying the further evolved target gene is produced. The host bacterium S2 may contain the helper plasmid CCP2 that supports the proliferation of post-evolution phage LWSe, the helper plasmid CCP3 that inhibits the proliferation of pre-evolution LWS, and the mutagenesis plasmid IMP2. The host bacterium S3 may contain the helper plasmid CCP2 that supports the proliferation of post-evolution phage LWSe, the helper plasmid CCP4 that inhibits the proliferation of pre-evolution LWS, and the mutagenesis plasmid IMP2. The function of the evolved target gene is at least partially linked to the function of the gene element on CCP2 that supports the proliferation of post-evolution LWSe. The function of the gene elements on CCP3 and CCP4 is linked to the function of the target gene before evolution. In addition, the gene elements carried by CCP3 and CCP4 have functional defects and cannot support the proliferation of pre-evolution LWS. This operation may reduce the wild-type activity of the target gene on the LWSeN. Thus, when the wild-type activity of the target gene in the LWSeN is reduced to a sufficient low level, the LWSeN may be able to use CCP2 to perform efficient infection and replication in S2. Efficient infection and replication of the phages may inhibit the growth of host bacteria, resulting in a clear infection spot visible to the naked eye that contains fewer bacteria formed in the LWSeN infected area. Depending on this infection spot, the evolution effect can be directly analyzed. CCP4 is a high-copy plasmid with even higher levels of expression of defective gene elements. Thus, CCP4 is an enhanced version of CCP3. The S3 host bacterium is used to replace the S2 host bacterium to further evolve the phage evolved in the S2 host bacterium. Similarly, the CCP2 plasmid has a lower copy number than that of CCP1. The low-copy CCP2 has a relatively low level of background expression, and so cannot support the proliferation of pre-evolution LWS, thus providing a stronger evolutionary selection pressure.

In addition, during the continuous outward movement of the host bacteria, the phages carrying the wild-type target gene activity that have low proliferation efficiency and that are in a low content may be eluted. Furthermore, by observing the size of the evolutionary infection spots, the plaque counts, or by real-time monitoring of the reporter gene, the activity of the target gene and the phage proliferation activity may be shown.

CCP2.1 is obtained by transforming T3 on CCP2 that controls the gIII into the T7 promoter. The host bacterium S4 carries CCP 2, and the host bacterium S5 carries CCP2.1. The present disclosure compares the T7 and T3 polymerase activities of the evolved target gene on LWSeN based on the difference in the number of plaques formed by the post-evolution phage LWSeN in S4 and S5 hosts.

The following will take the evolution of the T7 RNA polymerase gene—T7 RNAP—that recognizes the T7 promoter (SEQ ID NO: 1) to the T3 polymerase gene—T3 RNAP—that recognizes the T3 promoter (SEQ ID NO: 2) as an example to describe the present disclosure in further detail. However, the protection under the present disclosure will not be limited to the evolution of the T7 RNA polymerase gene. The T3 polymerase mentioned here refers to a polymerase obtained through evolution experiments that can functionally recognize the T3 promoter, but does not necessarily mean that this polymerase has the same gene sequence as the natural T3 RNA polymerase. The target gene to be evolved on the phage LWS is the T7 RNA polymerase gene. Expression of the gIII on the helper plasmid CCP1 (SEQ ID NO: 3) is controlled by the T3 promoter. Expression of the gIII on the helper plasmid CCP2 (SEQ ID NO: 4) is controlled by the T3 promoter. Expression of the gIII on the helper plasmid CCP2.1 (SEQ ID NO: 6) is controlled by the T7 promoter. Expression of the gIII-neg on the helper plasmid CCP3 (SEQ ID NO: 5) is controlled by the T7 promoter. And expression of the gIII-neg on the helper plasmid CCP4 is controlled by the T7 promoter. The gIII-neg is a defective-type of gIII, which lacks about 70 amino acids between aa280 and aa350 of the gIII, and so cannot support the proliferation and evolution of LWS. When expressed together with gIII, gIII-neg may competitively inhibit LWS proliferation.

In the present disclosure, the phage LWS and the helper plasmid CCP4 are respectively the same as the phage SM and the HP4 disclosed in Chinese Patent Application Number 201610349254.3.

Expression of the mutagenic gene on the mutant plasmid IMP1 is controlled by the T7 promoter. The mutagenesis plasmid IMP2 differs from the mutagenesis plasmid IMP1 in that the expression of the mutagenic gene is controlled by the T3 promoter, where the gene sequence of the mutagenesis plasmid IMP2 is shown as SEQ ID NO: 7. The mutagenesis plasmid IMP3 differs from the mutagenesis plasmid IMP2 in that the expression of the mutagenic gene on the mutagenesis plasmid IMP3 is controlled by the psp promoter. The bacteriophage M13-WT is a wild-type bacteriophage obtained by inserting a gene into the M13KO7 phage purchased from NEB. Compared with the bacteriophage LWS, the genomes and functions of M13-WT (NCBI ACCESSION: V00604) and T7 bacteriophage (NCBI ACCESSION: NC_001604) are complete, and they are able to independently infect and proliferate in the host bacteria.

Part of the bacteriophages and plasmids in the present disclosure are obtained by inventors' further modification of some materials provided by David R Liu laboratory. There has been relevant literature reporting its genetic information (Nat Chem Biol. 2014 March; 10 (3): 216-222). Other plasmids and bacterial strains are obtained through construction by the Applicants. The host bacterium used in this disclosure is E. coli M15, which is obtained by introducing F plasmid into E. coli MG1655 of the E. coli K12 series. The genotype is F'proA+B+lacIq Δ(lacZ)M15 zzf::Tn10(TetR)/attB::aph tetR.

It should be noted that the host bacterium used in this disclosure will not be limited to E. coli M15, it may be any E. coli carrying F factor. Furthermore, the E. coli M15, LWS, CCP1, CCP2, CCP2.1, CCP3, CCP4, IMP1, IMP2, IMP3 (FIGS. 4-12) may all be obtained by conventional molecular cloning methods such as PCR, enzyme cutting and ligation, and gene recombination, in connection with the gene maps and sequences. Molecular cloning methods such as gene recombination, PCR, and enzyme cutting and ligation are techniques well known in the art, and it has been established that corresponding strains, plasmids, and phages can be obtained by these methods. Thus, the host bacteria, plasmids, and phages as used herein have reproducible characteristics, and those skilled in the art may obtain them using conventional methods. Accordingly, those skilled in the art will appreciate that the present disclosure can satisfy the requirements for sufficiency of disclosure without providing bacterial species preservation.

In this disclosure, the host bacteria carrying CCP1 and IMP1 are called S1, the host bacteria carrying IMP2, CCP2, and CCP3 are called S2, and the host bacteria carrying IMP2, CCP2, and CCP4 are called S3. In positive screening, the initial LWS undergoes continuous directed evolution in S1 bacteria. The initial LWS carries the T7 RNAP gene, and may only use the background expression of CCP1 in S1 bacterium to perform low-level proliferation and mutation and evolution. As T7RNAP carried by LWS continues to evolve towards T3RNAP, an LWS mutant strain capable of activating the expression of gIII on CCP1 that is controlled by T3 promoter may be produced. This mutant strain may be able to further carry out a relatively high level of proliferation and evolution in S1 bacteria, and continuously improve its activity of activating the gIII in CCP1 that is controlled by the T3 promoter, thus obtaining the mutant bacteriophage LWSe and the target gene evolved into pre-T3RNAP (Sub-figure a of FIG. 2). This process is called positive screening.

After evolution, the pre-T3RNAP on LWSe may have a relatively high activity on both T7 and T3 promoters. In order to improve the specificity of pre-T3RNAP for T3 promoter, it is needed to evolve and screen out the T3RNAP with low ability to recognize and activate the T7 promoter. This process is called negative screening.

Negative screening needs to use CCP3 or CCP4. When the LWSe evolved through positive screening infects the S2 bacterium, the evolved target gene pre-T3RNAP on LWSe is able to turn on the expression of gIII-R5, which may inhibit its proliferation. This situation will last until LWSe has evolved some new bacteriophage mutants. The target genes carried by these new bacteriophage mutants may efficiently activate the expression of the gIII on CCP2 controlled by the T3 promoter while may not or rarely activate the expression of the gIII-R5 gene on CCP3 or CCP4 that is controlled by the T7 promoter. Then, these new bacteriophage mutants may continue to evolve in S2 or S3 strains, thus finally obtaining the evolved phage LWSeN carrying the highly specific T3 RNA polymerase gene—T3RNAP (Sub-figure b of FIG. 2). CCP4 is a high-copy plasmid with even higher levels of expression of defective gene elements. Thus, CCP4 is an enhanced version of CCP3. The S3 host bacterium is used to replace the S2 host bacterium, and the phages that have been evolved in S2 host bacterium may be transferred to S3 host bacterium for further evolution.

The implementation of the present disclosure will now be illustrated through the following embodiments. It should be noted however, that the following embodiments are merely exemplary, and are intended for the mere purpose of illustrating the implementation of the present disclosure, rather than restricting the scope of the protection of this disclosure.

EMBODIMENT 1

The following preparations need to be done before the evolution experiments.

1) Incubate host bacterium S1 carrying CCP1 and IMP1 plasmids in LB (Lysogeny broth) culture medium containing 50 ug/ml tetracycline, 50 µg/ml spectinomycin, and 25 µg/ml chloramphenicol under conditions of 37° C. and 220 rpm until OD600=0.3. Then dilute S1 by a factor of 100, and incubate it again under the same culture conditions until OD600=0.3. After two rounds of incubation, the host bacterium S1 can be used for evolution experiments.

2) Incubate host bacterium S2 carrying CCP2, CCP3, and IMP2 plasmids in LB culture medium containing 50 ug/ml tetracycline, 50 µg/ml spectinomycin, 50 µg/ml carbenicillin, and 25 µg/ml chloramphenicol under conditions of 37° C. and 220 rpm until OD600=0.3. Then dilute S2 by a factor of 100, and incubate it again under the same culture conditions until OD600=0.3. After two rounds of incubation, the host bacterium S2 can be used for evolution experiments.

3) Incubate host bacterium S3 carrying CCP2, CCP4, and IMP2 plasmids in LB culture medium containing 50 ug/ml tetracycline, 50 µg/ml spectinomycin, 50 µg/ml carbenicillin, and 25 µg/ml chloramphenicol under conditions of 37° C. and 220 rpm until OD600=0.3. Then dilute S3 by a factor of 100, and incubate it again under the same culture conditions until OD600=0.3. After two rounds of incubation, the host bacterium S3 can be used for evolution experiments.

4) Incubate host bacterium S4 carrying CCP2 in LB culture medium containing 50 ug/ml tetracycline and 50 µg/ml carbenicillin under conditions of 37° C. and 220 rpm until OD600=0.3. Then dilute S4 by a factor of 100, and incubate it again under the same culture conditions until OD600=0.3. After two rounds of incubation, the host bacteria S4 can be used for evolution experiments.

5) Incubate host bacterium S5 carrying CCP2.1 in LB culture medium containing 50 ug/ml tetracycline and 50 µg/ml carbenicillin under conditions of 37° C. and 220 rpm until OD600=0.3. Then dilute S5 by a factor of 100, and incubate it again under the same culture conditions until OD600=0.3. After two rounds of incubation, the host bacterium S5 can be used for evolution experiments.

6) Incubate host bacterium S6 carrying CCP1 in LB culture medium containing 50 ug/ml tetracycline and 50 µg/ml spectinomycin under conditions of 37° C. and 220 rpm until OD600=0.3. Then dilute S6 by a factor of 100, and incubate it again under the same culture conditions until OD600=0.3. After two rounds of incubation, the host bacterium S6 can be used for evolution experiments.

7) Incubate host bacterium S7 carrying IMP3 and CCP1 in LB culture medium containing 50 ug/ml tetracycline, 50 ug/ml spectinomycin, and 25 µg/ml chloramphenicol under conditions of 37° C. and 220 rpm until OD600=0.3. Then dilute S7 by a factor of 100, and incubate it again under the same culture conditions until OD600=0.3. After two rounds of incubation, the host bacterium S7 can be used for evolution experiments.

8) Incubate E. coli M15 in LB culture medium containing 50 ug/ml tetracycline under conditions of 37° C. and 220 rpm until OD600=0.3. Then dilute E. coli M15 by a factor of 100, and incubate it again under the same culture conditions until OD600=0.3. After two rounds of incubation, the E. coli M15 can be used for evolution experiments.

9) Incubate E. coli MG1655 in LB culture medium under conditions of 37° C. and 220 rpm until OD600=0.3. Then dilute E. coli MG1655 by a factor of 100, and incubate it again under the same culture conditions until OD600=0.3. After two rounds of incubation, the E. coli MG1655 can be used for evolution experiments.

EMBODIMENT 2

Method of Observing LWS Plaques in S4 or S5 Host Bacteria

1) Lay a layer of 10 ml of 1.5% agarose gel onto a 10 cm bacterial culture plate, and leave it at room temperature for 20 min to allow it to solidify.

2) When the concentration of bacteriophages LWS is unknown, the LWS needs to be diluted at each of serial dilution gradients of factors of $10^{1, 2, 3, 4, 5, 6, 7, 8, 9}$.

3) Take multiple groups of 200 µL of S4 or S5 host bacteria prepared in "Embodiment 1", add 10 µL of LWS with different dilution gradients prepared in "2)" into the respective multiple groups, and then add 4 ml of LB medium that is stored at 55° C. and that contains 0.4% bacteriological agar as well as carbenicillin at a final concentration of 50 µg/ml. Mixing them evenly in a vortex mixer, spread the sample on the plate prepared in "1)". Then leave them at room temperature for 1 h to allow it to solidify.

4) Incubate them overnight in a 37° C. biochemical incubator.

5) Observe and count the number of plaques formed by each gradient dilution sample, and calculate the LWS concentration of the original sample.

The gIII on CCP2.1 carried by S5 is activated by the T7 promoter, and so the bacteriophage LWS carrying the T7 RNAP target gene may form plaques in the S5 host bacteria. In contrast, the gIII on CCP2 carried by S4 is activated by the T3 promoter, and only the LWSe of which the carried target gene has been evolved with the T3 RNAP activity can form plaques in the S4 host bacteria. Comparing the changes in the number of plaques formed by LWSe in S4 and S5 host bacteria, the evolution effect of LWSe may be directly analyzed.

EMBODIMENT 3

Host Bacteria and Bacteriophage Infection and Movement Test

1) Add 10 ml of LB culture medium containing 0.25% bacteriological agar onto a 10 cm bacterial culture plate. The culture medium contains 50 µg/ml tetracycline and 50 µg/ml carbenicillin. Leave them at room temperature for 1 h to allow it to solidify.

2) As illustrated in FIG. 1a, inoculate 2 µl of the host bacteria S5 prepared in "Embodiment 1" onto the surface at the center of the plate. Inoculate 2 µl of LWS phage with a titer of $10^6$ pfu/ml at each of three outside corners 1 cm away from the S5 inoculation site.

3) Incubate the plate overnight in a 37° C. biochemical incubator. Later, the phenomenon illustrated in Sub-figure b of FIG. 1 may be observed. The host bacteria moves from the center to the edge, and the host bacteria in motion then come into contact with the phages and are infected by the phages to produce progeny phages, while continuing to move towards the outer edge. Because infected host bacteria grow slower hence a relatively small number of bacteria while the host bacteria in the uninfected area maintain their original state hence a relatively larger number of bacteria, a clear V-shaped infection spot containing fewer bacteria may be seen in the infected area. The presence of this clear infection spot could be used to indicate the presence of phage infection, and the degree of transparency and size of the clear infection spot may represent the infectious activity of the phages.

EMBODIMENT 4

SPACE Positive Screening Evolution

1) First round of evolution: prepare three 10 cm bacterial culture plates a, b, and c, and add 10 ml of LB culture medium containing 0.25% bacteriological agar to each of the three culture plates, where culture medium contains 50 μg/ml tetracycline and 50 μg/ml spectinomycin. Leave them at room temperature for 1 h to allow them to solidify.

Then prepare four 10 cm bacterial culture plates d, e, f, and g, and add 10 ml of LB culture medium containing 0.25% bacteriological agar to each of the fourth culture plates, where the culture medium contains 50 μg/ml tetracycline, 50 μg/ml spectinomycin, and 25 μg/ml chloramphenicol. Leave them at room temperature for 1 h to allow them to solidify.

2) As illustrated in FIG. 1a, inoculate 2 μl of the host bacteria S6 prepared in "Embodiment 1" onto the surface at the center of each of the three plates a, b, and c. Inoculate 2 μl of LWS phage with a titer of $10^8$ pfu/ml at each of three outside corners 1 cm away from the S6 inoculation site on plate a. Inoculate 2 μl of LWS phage with a titer of $10^9$ pfu/ml at each of three outside corners 1 cm away from the S6 inoculation site on plate b. Inoculate 2 μl of LWS phage with a titer of 1010 pfu/ml at each of three outside corners 1 cm away from the S6 inoculation site on plate c.

Inoculate 2 μl of the host bacteria S1 prepared in "Embodiment 1" on the surface at the center of each of the four plates d, e, f, and g. Inoculate 2 μl of LWS phage with a titer of $10^8$ pfu/ml at each of three outside corners 1 cm away from the S1 inoculation site on plate d. Inoculate 2 μl of LWS phage with a titer of $10^9$ pfu/ml at each of three outside corners 1 cm away from the S1 inoculation site on plate e. Inoculate 2 μl of LWS phage with a titer of 1010 pfu/ml at each of three outside corners 1 cm away from the S1 inoculation site on plate f. The g plate is not inoculated with phages.

The d, e, f plates are SPACE evolution groups added with different amounts of initial phages. The a, b, and c plates are control groups at different phage addition levels without adding the mutagenesis plasmid IMP1. The g-plate is a negative control group containing no phages.

3) Incubate the plates overnight in a 37° C. biochemical incubator.

4) The effects of a-g plates after incubation are illustrated in FIGS. 4a-g. The S6 host bacteria in the a, b, and c plates do not carry mutagenesis plasmids, and so the phages do not undergo mutation and evolution. On the a, b, and c plates, the bacteriophage LWS can only rely on the background expression of CCP1 for weak proliferation, and will soon be left behind by the moving host bacteria, making it not sufficient to form visible infection spots. The final result is the same as in negative control group g.

The host bacterium S1 on the d, e, and f plates carries the mutagenesis plasmid IMP1. Thus, although at the beginning the bacteriophage LWS can only use the CCP1 background expression for proliferation, the bacteriophage LWS is able to activate the mutagenic gene on IMP1 thus assisting itself to mutate and evolve the T3RNAP activity. Thus, infection spots may be quickly formed on d, e, f plates, and the larger the amount of phages initially added, the more obvious the infection spots.

Infection spots are obvious on the e-plate, and no non-specific infection spots are seen on the b-plate added with the same amount of initial phages LWS as e plate. Therefore, the follow-up embodiments chose e plate for experimental analysis.

The evolved or post-evolution bacteriophage LWSe exists in the infection spots evolved on the e plate. A 5 μl sample is taken at each of the starting point α (near the center of the plate), the middle point β, and the end point γ (away from the center of the plate) of an infection spot on the e plate, and these samples are marked as LWSeα, LWSeβ, LWSeγ, respectively. The samples are each diluted by a factor of 100 using LB liquid culture medium, and then mixed evenly in a vortex mixer for 2 minutes. The samples uniformly mixed are then filtered using a 0.22 μm syringe filter, and the formation of the T3 plaque in S4 bacteria in which the expression of the gIII is controlled by the T3 promoter, together with the formation of the T7 plaque in S5 bacteria in which the expression of the gIII is controlled by the T7 promoter are detected in each of the samples LWSeα, LWSeβ, and LWSeγ, according to the method described in the "Embodiment 2".

As illustrated in FIG. 4h, the pre-evolution bacteriophage LWS carries the wild-type T7 RNAP gene and can only form T7 plaque in the host bacteria S5, but cannot form T3 plaque in the host bacteria S4. As evolution progresses, the bacteriophage LWS becomes the bacteriophage LWSe. The target gene carried on LWSe is constantly mutated, so that it starts to have T3 RNAP activity and is able to recognize the T3 promoter, and so can form T3 plaque in the host bacteria S4. And the farther away from the center of the plate, the longer the evolution time, the better the evolution effect, and the more obvious the T3 RNAP activity acquired by LWSe. As illustrated in FIG. 4h, the ability to form T3 plaque in S4 from is becoming increasingly stronger from LWS to LWSeγ. Therefore, in the follow-up embodiments, the sample at the endpoint of the infection spot far away from the center of the plate after each evolution would be taken and diluted by a factor of 100, and then filtered using a 0.22 μm syringe filter, and then further analyzed or subjected to further evolution.

For consistency with the follow-up embodiments, the LWSeγ sample will later be relabeled as LWSe1, where "1" represents one round of evolution. Therefore, in the present disclosure, LWSe1 and LWSeγ represent the names of the same sample in different scenarios.

Second round of evolution: on the same plate, inoculate S1 host bacterium onto the center of the plate, and then inoculate 2 μl of the filtered bacteriophage LWSe1 at each of three outer corners 1 cm away from the S1 inoculation site, so as to perform the second round of evolution under the same conditions.

Figure 5:
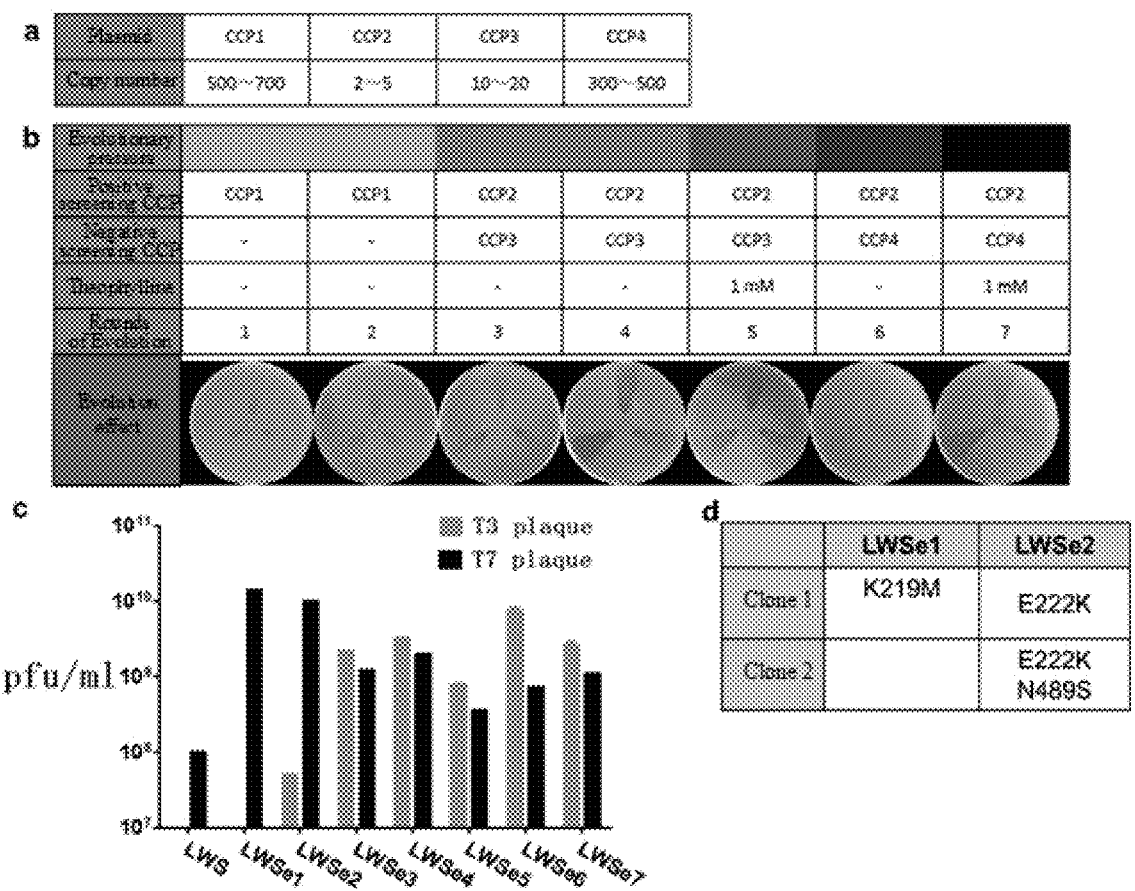
FIG. 5 is a diagram illustrating the evolution results of multiple rounds of SPACE in accordance with Embodiment 5 and Embodiment 6 of the present disclosure.

Take 5 μl of LWSe2 phage sample from at the endpoint of the plaque formed at the second round of evolution and dilute it by a factor of 100, then filter it with a 0.22 μm syringe filter, and then detect the formation of the T3 plaque in S4 host bacteria and the formation the T7 plaque in S5 host bacteria. As illustrated in FIG. 5, after an additional round of evolution, LWSe2 has a stronger ability to form T3 plaque in S4 host bacteria than LWSe1.

EMBODIMENT 5

SPACE Negative Screening Evolution Under S2 or S3 Host Bacteria

1) Third round of evolution: add 10 ml of LB culture medium containing 0.25% bacteriological agar to a 10 cm culture plate, where the culture medium contains 50 μg/ml tetracycline, 50 μg/ml carbenicillin, 50 μg/ml spectinomycin, and 25 μg/ml chloramphenicol. Leave the culture pate with the LB culture medium at room temperature for 1 h to allow the culture medium to solidify. In addition to the T7 promoter, there is a riboswitch inducible by theophylline on the CCP3 and CCP4 plasmids carried by S2. However, this riboswitch is not strict, and there is still a certain gIII-neg background expression without adding theophylline, so that the proliferation of the bacteriophage LWSe carrying the target gene having wild-type T7 RNAP activity is repressed.

Then inoculate 2 μl of host bacteria S2 onto the center of the plate, and then inoculate 2 μl of the filtered phage LWSe2 at each of three outer corners of a triangle that are 1 cm away from the S2 inoculation site, and incubate them in a 37° C. incubator overnight. The third round of evolution begins.

Take 5 μl of LWSe3 phage sample from the endpoint of the infection spot formed during the third round of evolution and dilute it by a factor of 100, then filter it with a 0.22 μm syringe filter, and then separately detect the formation of T3 plaque in S4 host bacteria and the formation of T7 plaque in S5 host bacteria.

2) Fourth round of evolution: The fourth round of evolution of the filtered LWSe3 sample is carried out using the same conditions as in step "1)" of this embodiment. Similarly, take 5 μl of LWSe4 phage sample from the endpoint of the infection spot formed during the fourth round of evolution and dilute it by a factor of 100, then filter it with a 0.22 μm syringe filter, and then separately detect the formation of T3 plaque in S4 host bacteria and the formation of T7 plaque in S5 host bacteria.

3) Fifth round of evolution: add 10 ml of LB culture medium containing 0.25% bacteriological agar to a 10 cm culture plate, where the culture medium contains 50 μg/ml tetracycline, 50 μg/ml carbenicillin, 50 μg/ml spectinomycin, 25 μg/ml chloramphenicol, and 1 mM theophylline. Leave them at room temperature for 1 h to allow the culture medium to solidify. Adding theophylline may increase the expression of gIII-neg on CCP3 and CCP4 thus increasing the evolutionary screening pressure.

Then inoculate 2 μl of host bacteria S2 onto the center of the plate, and then inoculate 2 μl of the filtered phage LWSe4 at each of three outer corners of a triangle that are 1 cm away from the S2 inoculation site, and incubate them in a 37° C. incubator overnight. The fifth round of evolution begins.

Take 5 μl of LWSe5 phage sample from the endpoint of the infection spot formed during the fifth round of evolution and dilute it by a factor of 100, then filter it with a 0.22 μm syringe filter, and then separately detect the formation of T3 plaque in S4 host bacteria and the formation of T7 plaque in S5 host bacteria.

4) Sixth round of evolution: add 10 ml of LB culture medium containing 0.25% bacteriological agar to a 10 cm culture plate, where the culture medium contains 50 μg/ml tetracycline, 50 μg/ml carbenicillin, 50 μg/ml spectinomycin, and 25 μg/ml chloramphenicol. Leave them at room temperature for 1 h to allow the culture medium to solidify.

Then inoculate 2 μl of host bacteria S3 onto the center of the plate, and then inoculate 2 μl of the filtered phage LWSe5 at each of three outer corners of a triangle that are 1 cm away from the S3 inoculation site, and incubate them in a 37° C. incubator overnight. The sixth round of evolution begins.

Take 5 μl of LWSe6 phage sample from the endpoint of the infection spot formed during the sixth round of evolution and dilute it by a factor of 100, then filter it with a 0.22 μm syringe filter, and then separately detect the formation of T3 plaque in S4 host bacteria and the formation of T7 plaque in S5 host bacteria.

5) Seventh round of evolution: add 10 ml of LB culture medium containing 0.25% bacteriological agar to a 10 cm culture plate, where the culture medium contains 50 μg/ml tetracycline, 50 μg/ml carbenicillin, 50 μg/ml spectinomycin, 25 μg/ml chloramphenicol, and 1 mM theophylline. Leave them at room temperature for 1 h to allow the culture medium to solidify.

Then inoculate 2 μl of host bacteria S3 onto the center of the plate, and then inoculate 2 μl of the filtered phage LWSe6 at each of three outer corners of a triangle that are 1 cm away from the S3 inoculation site, and incubate them in a 37° C. incubator overnight. The seventh round of evolution begins.

Take 5 μl of LWSe7 phage sample from the endpoint of the infection spot formed during the seventh round of evolution and dilute it by a factor of 100, then filter it with a 0.22 μm syringe filter, and then separately detect the formation of T3 plaque in S4 host bacteria and the formation of T7 plaque in S5 host bacteria.

Effects of the total 7 rounds of evolution are illustrated in FIG. 5. Sub-figure a of FIG. 5 shows the copy numbers of different CCPs. The copy number affects the level of gene expression and the selection pressure during evolution. Sub-figure b of FIG. 5 shows the effect of each round of evolution on the plate, where the evolutionary pressure row uses light to dark filling colors to indicate weak to strong evolutionary selection pressures due to different evolutionary conditions. Sub-figure c of FIG. 5 shows the effect of plaque formation in S4 and S5 host bacteria by the evolved product generated in each round. As illustrated in the figure, as the number of evolution rounds increases, the selection pressure in the evolution process is getting increasingly stronger, and the evolution effect is becoming more and more obvious. The LWS bacteriophage carrying wild-type T7 RNAP gene can only form T7 plaques in S5 host bacteria in which the gIII expression is controlled by the T7 promoter, but cannot form T3 plaques in S4 host bacteria where the gIII expression is controlled by the T3 promoter. As evolution progresses, in the direction of LWSe1 to LWSe7 bacteriophages, their ability of forming T7 plaques in S5 host bacteria is overall getting increasingly weaker, but their ability of forming T3 plaques in S4 host bacteria is becoming increasingly stronger.

EMBODIMENT 6

SPACE Product Sequencing Analysis

Each of the first two rounds of evolutionary products, namely the phages LWSe1 and LWSe2, are purified to obtain several clones for target gene sequencing. As illustrated in Sub-figure d of FIG. 5, the target genes they carry are both directly mutated at amino acids 1-310 at the N-terminal. There have been reports showing that this region is related to the recognition of the promoter by T7 RNAP. One example is that the E222K mutation has been reported by David R Liu to affect the specificity of T7RNAP.

Based on the comparison of the bacteriophage's ability to form plaques in S5 and S4 host bacteria before and after evolution as well as the sequencing results, it can be seen that the change in the activity of the target gene carried by LWSe bacteriophage from 7RNAP to T3RNAP is due to mutations caused by SPACE evolution.

IMPLEMENTATION 1

IMP3 Inducing SPACE Evolution Test

1) Prepare three 10 cm bacterial culture plates a, b, and c. To each culture plate, add 10 ml of LB culture medium containing 0.25% bacteriological agar, where the culture medium contains 50 μg/ml tetracycline, 50 μg/ml spectinomycin, and 25 μg/ml chloramphenicol. Leave them at room temperature for 1 h to allow the culture medium to solidify.

2) As illustrated in Sub-figure a of FIG. 1, inoculate 2 μl of the host bacteria S7 prepared in Embodiment 1 onto the surface at the center of each of a and c plates. Inoculate 2 μl of LWS phage with a titer of $10^9$ pfu/ml at each of three outer corners 1 cm away from the inoculation site of the host bacteria S7 on plate a. Plate c is used as a negative group which is not inoculated with phages.

Inoculate 2 μl of the host bacteria S1 prepared in Embodiment 1 onto the surface at the center of plate b. Inoculate 2 μl of LWS phage with a titer of $10^9$ pfu/ml at each of three outer corners 1 cm away from the inoculation site of the host bacteria S1 on plate b.

3) Incubate the plates overnight in a 37° C. biochemical incubator.

Figure 6:
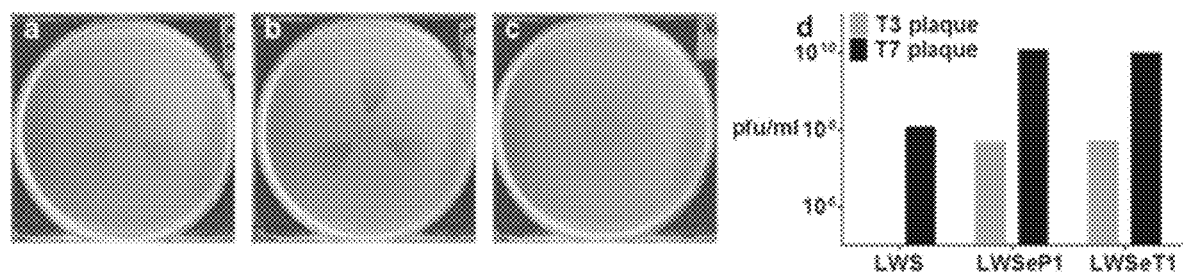
FIG. 6 shows a diagram illustrating the evolution effects of the SPACE induced by IMP3 and a bar graph depicting the counts of different bacteriophages in accordance with Implementation 1 of the present disclosure.
Figure 7:
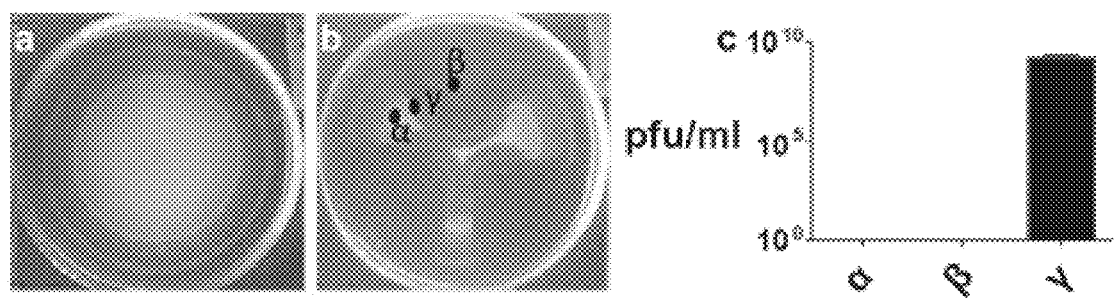
FIG. 7 shows a diagram illustrating the effects of the infection and movement of the T7 bacteriophage and a bar graph depicting the counts of bacteriophages in accordance with Implementation 2 of the present disclosure.

4) The effects of a-c plates after evolution are illustrated in Sub-figures a-c of FIG. 6. The host bacteria S7 carrying IPM3 and the host bacteria S1 carrying IMP1 have similar evolutionary infection spots. Take 5 μl of the post-evolution phage sample LWSeP1 from the endpoint of the evolutionary infection spot of the host bacteria S7 group and dilute it by a factor of 100, and then filter it using a 0.22 μm syringe filter. Then separately detect the formation of T3 plaque in S4 host bacteria and the formation of T7 plaque in S5 host bacteria.

Take 5 μl of the post-evolution phage sample LWSeT1 from the endpoint of the evolutionary infection spot of the host bacteria S1 group and dilute it by a factor of 100, and then filter it using a 0.22 μm syringe filter. Then separately detect the formation of T3 plaque in S4 host bacteria and the formation of T7 plaque in S5 host bacteria.

As illustrated in Sub-FIG. 6 of FIG. 6, the numbers of T3 and T7 plaques are similar between LWSeT1 and LWSeP1. This shows that the IMP3 controlled by psp operon has the same effect on promoting mutation and evolution as IMP1.

Therefore, it is known that IMP3 can be directly used to replace IMP1 and IMP2, so that the expression of IMP is separated from the activity of the target gene. In this case, regardless of whether it being positive screening or negative screening in evolutionary synthesis of the target gene, the same IMP3 may be used.

IMPLEMENTATION 2

Virulent Phage Infection and Movement Test

1) The above embodiments are based on chronic infectious M13 bacteriophage. However, the present disclosure may also be used for evolution experiments on other bacteriophages. Here, the virulent bacteriophage T7 is used as an example for illustration.

2) Add 10 ml of LB culture medium containing 0.25% bacteriological agar onto a 10 cm bacterial culture plate. Leave them at room temperature for 1 h allowing the culture medium to solidify.

3) As illustrated in Sub-figure a of FIG. 1, inoculate 2 μl of the host bacteria E. coli MG1655 prepared in "Embodiment 1" onto the surface at the center of the plate. Then inoculate 2 μl of T7 phages with titers of $10^4$, $10^5$, and $10^6$ pfu/ml respectively at three outer corners 1 cm away from the inoculation site of E. coli MG1655. The control group replaces the phage with LB culture medium.

4) Incubate the plates overnight in a 37° C. biochemical incubator. Later, the phenomenon shown in Sub-figure b of FIG. 7 may be observed. The host bacteria moves from the center to the edge, and the host bacteria in motion then come into contact with the phages and are infected by the phages to produce progeny phages, while continuing to move towards the outer edge. T7 bacteriophage is a virulent bacteriophage, and all infected host bacteria are lysed and killed. Therefore, V-shaped clear infection spots are formed on the plates. There is no bacteriophage in the control group Sub-figure a of FIG. 7, so no V-shaped infection spots are formed, and its bacteria are evenly distributed to form a circle. Regarding the group with an inoculation volume of $10^6$ pfu/ml, samples are taken at each of the α point of the infected area, the β point of the uninfected area, and the γ point of the interfacing area in Sub-figure b of FIG. 7, and the plaque counts are calculated according to "Embodiment 2" using E. coli MG1655. As illustrated in Sub-figure c of FIG. 7, T7 bacteriophage on the order of $10^9$ pfu/ml is measured at the γ point. It can be seen that the T7 virulent bacteriophage can also infect the host bacteria as the host bacteria move on the plate, and form infection spots visible to the naked eye as signs of infection. In view of this, the embodiments according to the present disclosure that are carried out on M13 phage may also be carried out on T7 phage.

In the foregoing embodiments, the evolution from the T7 RNA polymerase gene—T7RNAP—that recognizes the T7 promoter to the T3 RNA polymerase gene—T3 RNHP—that recognizes the T3 promoter is taken as an example for purposes of illustrating the present disclosure. Alternatively, other target genes (e.g., protease gene, cellulase gene, fluorescent protein gene, quorum-sensing gene, etc.) may also be used replace the T7RNHP gene in LWS, and the expression regulation and the post-expression modification of gIII and gIII-R5 genes in CCP1, CCP2, CCP3, and CCP4 plasmids may be adjusted accordingly so that the expression of gIII and gIII-R5 is linked to the biological activity of the new target gene to be evolved on LWS, then the present system can be used to conduct directed evolution of the new target gene.

Although the present disclosure has been illustrated and described in connection with specific embodiments and implementations, it is to be appreciated that many other changes and modifications can be made without departing from the spirit and scope of the present disclosure. All such changes and modifications falling in the scope of the present disclosure shall all be included in and by the appended claims.

What is claimed is:

1. A visual continuous spatial directed evolution method, comprising:
allowing a host to grow and move in a solid culture space, the host carrying a foreign target gene to be evolved, and the host itself containing a gene element that assists the evolution of the target gene, wherein the target gene is correlated with the growth and movement of the host; and
performing screening to obtain an evolved product depending on different spatial distribution patterns formed in the solid culture space during the process of growth and movement of the host,
wherein the target gene is located in a parasitic organism corresponding to the host and the parasitic organism is a bacteriophage.

2. The visual continuous spatial directed evolution method as recited in claim 1, wherein the host is a non-defective strain of a natural host bacterium of the bacteriophage.

3. The visual continuous spatial directed evolution method as recited in claim 1, wherein the host comprises *Escherichia coli*.

4. The visual continuous spatial directed evolution method as recited in claim 3, wherein the host is *Escherichia coli* carrying F factor (fertility factor).

5. The visual continuous spatial directed evolution method as recited in claim 1, wherein the bacteriophage is a temperate bacteriophage.

6. The visual continuous spatial directed evolution method as recited in claim 1, wherein the bacteriophage comprises a filamentous bacteriophage.

7. The visual continuous spatial directed evolution method as recited in claim 6, wherein the filamentous bacteriophage comprises M13 filamentous bacteriophage.

8. The visual continuous spatial directed evolution method as recited in claim 1, wherein the target gene comprises one or more coding sequences, wherein the one or more coding sequences code for one or more proteins.

9. The visual continuous spatial directed evolution method as recited in claim 8, wherein the target gene comprises T7 RNA polymerase gene.

10. The visual continuous spatial directed evolution method as recited in claim 1, wherein the gene element that assists the evolution of the target gene is a mutagenesis plasmid, and the expression of the mutagenesis plasmid is induced by one or more genes in a pre-evolution phage.

11. The visual continuous spatial directed evolution method as recited in claim 10, wherein the one or more genes in the pre-evolution phage comprises an exogenous gene that is introduced.

12. The visual continuous spatial directed evolution method as recited in claim 10, wherein the mutagenesis plasmid contains one or more mutagenic genes.

13. The visual continuous spatial directed evolution method as recited in claim 12, wherein the one or more mutagenic genes comprise a DNAQ gene mutant DNAQ926 gene in which the 12- and 14-position amino acids are each mutated to Ala.

14. The visual continuous spatial directed evolution method as recited in claim 1, wherein the solid culture space comprises a two-dimensional planar culture structure and a three-dimensional space culture structure, wherein the continuity of the movement and evolution in the vertical direction in the solid culture space is maintained by regularly forming a cast solid culture system;
and the directed evolution is a high-throughput evolution, which is achieved by using multiple sets of solid culture spaces.

15. The visual continuous spatial directed evolution method as recited in claim 1, wherein the target gene is correlated with the growth and movement of the host through a helper plasmid, the helper plasmid containing at least a first helper plasmid, the first helper plasmid being a helper plasmid CCP1, where the nucleic acid sequence of the helper plasmid CCP1 is shown in SEQ ID NO: 3.

16. The visual continuous spatial directed evolution method as recited in claim 15, wherein the helper plasmid further comprises a second helper plasmid, the second helper plasmid being helper plasmid CCP3, where the nucleic acid sequence of helper plasmid CCP3 is shown in SEQ ID NO: 5.

17. The visual continuous spatial directed evolution method as recited in claim 8, wherein the target gene is correlated with the growth and movement of the host through a helper plasmid, the helper plasmid containing at least a first helper plasmid, the first helper plasmid being a helper plasmid CCP1, where the nucleic acid sequence of the helper plasmid CCP1 is shown in SEQ ID NO: 3.

18. The visual continuous spatial directed evolution method as recited in claim 15, wherein the directed evolution is carried out using different hosts in succession, and a latter host contains genetic elements that support phage proliferation, the genetic elements comprising a helper plasmid that supports the proliferation of a post-evolution phage and a helper plasmid that inhibits the proliferation of a pre-evolution phage.

\* \* \* \* \*

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taatacgact cactataggg                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2 attaccctc actaaaggga                                                    20

<210> SEQ ID NO 3
<211> LENGTH: 3935
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ttgagatcct ttttttctgc gcatcgctga gataggtgcc tcactgatta agcattggta      60
actgtcagac caagtttact catatatact ttagattgat ttaaaacttc atttttaatt     120
taaaaggatc taggtgaaga tcctttttga taatctcatg accaaaatcc cttaacgtga     180
gttttcgttc cactgagcgt cagacccccgt agaaaagatc aaaggatctt cttgagatcc    240
ttgcggtggt ttgtttgccg gatcaagagc taccaactct ttttccgaag gtaactggct     300
tcagcagagc gcagatacca aatactgttc ttctagtgta gccgtagtta ggccaccact     360
tcaagaactc tgtagcaccg cctacatacc tcgctctgct aatcctgtta ccagtggctg     420
ctgccagtgg cgataagtcg tgtcttaccg ggttggactc aagacgatag ttaccggata     480
aggcgcagcg gtcgggctga acggggggtt cgtgcacaca gcccagcttg gagcgaacga     540
cctacaccga actgagatac ctacagcgtg agctatgaga aagcgccacg cttcccgaag     600
ggagaaaggc ggacaggtat ccggtaagcg gcagggtcgg aacaggagag cgcacgaggg     660
agcttccagg gggaaacgcc tggtatcttt atagtcctgt cgggtttcgc cacctctgac     720
ttgagcgtcg atttttgtga tgctcgtcag ggggcggag cctatggaaa aacgccagca     780
acgcggcctt tttacggttc ctggcctttt gctggccttt tgctcacatg ttctttcctg     840
cgttatcccc tgattctgtg gataaccgta ttaccgcctt tgagtgagct gataccgctc     900
gccgcagccg aacgaccgag cgcagcgagt cagtgagcga ggaagcggaa gagcgcccaa     960
tacgcaaacc gcctctcccc gcgcgttggc cgattcatta atgcagctgg cacgacaggt    1020
ttcccgactg gaaagcgggc agtgagcgca acgcgtcaag aggacatccg gtcaaataaa    1080
acgaaaggct cagtcgaaag actgggcctt tcgttttgct gaggagactt agggacccta    1140
caattaaccc tcactaaagg gagaaagacc tgcaggtgca gtaaggagga tatataaaaa    1200

```
aaaatgaaaa aattattatt cgcaattcct ttagttgttc ctttctattc tcactccgct    1260
gaaactgttc atcaccatca ccatcacgct gaaactgttg aaagttgttt agcaaaaccc    1320
catacagaaa attcatttac taacgtctgg aaagacgaca aaactttaga tcgttacgct    1380
aactatgagg gctgtctgtg gaatgctaca ggcgttgtag tttgtactgg tgacgaaact    1440
cagtgttacg gtacatgggt tcctattggg cttgctatcc ctgaaaatga gggtggtggc    1500
tctgagggtg gcggttctga gggtggcggt tctgagggtg gcggtactaa acctcctgag    1560
tacggtgata cacctattcc gggctatact tatatcaacc ctctcgacgg cacttatccg    1620
cctggtactg agcaaaaccc cgctaatcct aatccttctc ttgaggagtc tcagcctctt    1680
aatactttca tgtttcagaa taataggttc cgaaataggc agggggcatt aactgtttat    1740
acgggcactg ttactcaagg cactgacccc gttaaaactt attaccagta cactcctgta    1800
tcatcaaaag ccatgtatga cgcttactgg aacggtaaat tcagagactg cgctttccat    1860
tctggcttta atgaggatcc attcgtttgt gaatatcaag gccaatcgtc tgacctgcct    1920
caacctcctg tcaatgctgg cggcggctct ggtggtggtt ctggtggcgg ctctgagggt    1980
ggtggctctg agggtggcgg ttctgagggt ggcggctctg agggaggcgg ttccggtggt    2040
ggctctggtt ccggtgattt tgattatgaa aagatggcaa acgctaataa gggggctatg    2100
accgaaaatg ccgatgaaaa cgcgctacag tctgacgcta aaggcaaact tgattctgtc    2160
gctactgatt acggtgctgc tatcgatggt ttcattggtg acgtttccgg ccttgctaat    2220
ggtaatggtg ctactggtga ttttgctggc tctaattccc aaatggctca agtcggtgac    2280
ggtgataatt cacctttaat gaataatttc cgtcaatatt accttccct  ccctcaatcg    2340 gttgaatgtc gccctttgt ctttggcgct ggtaaacctt acgagttcag tatcgactgc    2400
gataagatca acctgttccg cggtgtcttt gcgtttcttt tatatgttgc cacctttatg    2460
tatgtatttt ctacgtttgc taacatactg cgtaataagg agtcttaatc atgaccatga    2520
ttacggattc actggccgtc gttttacaac gtcgtgactg ggaaaaccct ggcgttaccc    2580
aacttaatcg ccttgcagca catccccctt tcgccagctg gcgtaatagc gaagaggccc    2640
gcaccgatcg cccttcccaa cagttgcgca gcctgaatgg cgaatggcgc tttgcctggt    2700
ttccggcacc agaagcggtg ccggaaagct ggctggagtg cgatcttcct gaggccgata    2760
ctgtcgtcgt cccctcaaac tggcagatgc acggttacga tgcgcccatc tacaccaacg    2820
tgacctatcc cattacggtc aatccgccgt ttgttcccac ggagaatccg acgggttgtt    2880
actcgctcac atttaatgtt gatgaaagct ggctacagga aggccagacg cgaattattt    2940
ttgatggcgt taactcggcg taaacttaat taacggcact cctcagcaaa tataatgacc    3000
ctcttgataa cccaagaggg catttttaa tgcccatggc gtttatttgc cgactacctt    3060
ggtgatctcg cctttcacgt agtggacaaa ttcttccaac tgatctgcgc gcgaggccaa    3120
gcgatcttct tcttgtccaa gataagcctg tctagcttca agtatgacgg gctgatactg    3180
ggccggcagg cgctccattg cccagtcggc agcgacatcc ttcggcgcga ttttgccggt    3240
tactgcgctg taccaaatgc gggacaacgt aagcactaca tttcgctcat cgccagccca    3300
gtcgggcggc gagttccata gcgttaaggt ttcatttagc gcctcaaata gatcctgttc    3360
aggaaccgga tcaaagagtt cctccgccgc tggacctacc aaggcaacgc tatgttctct    3420
tgcttttgtc agcaagatag ccagatcaat gtcgatcgtg gctggctcga agatacctgc    3480
aagaatgtca ttgcgctgcc attctccaaa ttgcagttcg cgcttagctg gataacgcca    3540
cggaatgatg tcgtcgtgca caacaatggt gacttctaca gcgcggagaa tctcgctctc    3600
```

```
tccaggggaa gccgaagttt ccaaaaggtc gttgatcaaa gctcgccgcg ttgtttcatc    3660
aagccttacg gtcaccgtaa ccagcaaatc aatatcactg tgtggcttca ggccgccatc    3720
cactgcggag ccgtacaaat gtacggccag caacgtcggt tcgagatggc gctcgatgac    3780
gccaactacc tctgatagtt gagtcgatac ttcggcgatc accgcttccc tcatactctt    3840 ccttttcaa tattattgaa gcatttatca gggttattgt ctcatgagcg gatacatatt     3900
tgaatgtatt tagaaaaata ggccaaatag gccgt                               3935
```

<210> SEQ ID NO 4
<211> LENGTH: 5320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ttttgctgag gagacttagg gaccctacaa ttaaccctca ctaaagggag aaagacctgc    60
aggtgcagta aggaggaaaa aaaaatgaaa aaattattat tcgcaattcc tttagttgtt    120
cctttctatt ctcactccgc tgaaactgtt catcaccatc accatcacgc tgaaactgtt    180
gaaagttgtt tagcaaaacc ccatacagaa aattcattta ctaacgtctg gaaagacgac    240
aaaactttag atcgttacgc taactatgag ggctgtctgt ggaatgctac aggcgttgta    300
gtttgtactg gtgacgaaac tcagtgttac ggtacatggg ttcctattgg gcttgctatc    360
cctgaaaatg agggtggtgg ctctgagggt ggcggttctg agggtggcgg ttctgagggt    420
ggcggtacta aacctcctga gtacggtgat acacctattc cgggctatac ttatatcaac    480
cctctcgacg gcacttatcc gcctggtact gagcaaaacc ccgctaatcc taatccttct    540
cttgaggagt ctcagcctct taatactttc atgtttcaga ataataggtt ccgaaatagg    600
cagggggcat taactgttta cgggcact gttactcaag gcactgaccc cgttaaaact     660
tattaccagt acactcctgt atcatcaaaa gccatgtatg acgcttactg aacggtaaa     720 ttcagagact gcgcttttcca ttctggcttt aatgaggatc cattcgtttg tgaatatcaa    780
ggccaatcgt ctgacctgcc tcaacctcct gtcaatgctg gcggcggctc tggtggtggt    840
tctggtggcg gctctgaggg tggtggctct gagggtggcg gttctgaggg tggcggctct    900
gagggaggcg gttccggtgg tggctctggt tccggtgatt ttgattatga aaagatggca    960
aacgctaata aggggggctat gaccgaaaat gccgatgaaa acgcgctaca gtctgacgct    1020
aaaggcaaac ttgattctgt cgctactgat tacggtgctg ctatcgatgg tttcattggt    1080
gacgtttccg gccttgctaa tggtaatggt gctactggtg attttgctgg ctctaattcc    1140
caaatggctc aagtcggtga cggtgataat tcacctttaa tgaataattt ccgtcaatat    1200
ttaccttccc tccctcaatc ggttgaatgt cgcccttttg tctttggcgc tggtaaacct    1260
tacgagttca gtatcgactg cgataagatc aacctgttcc gcggtgtctt tgcgtttctt    1320
ttatatgttg ccacctttat gtatgtattt tctacgtttg ctaacatact gcgtaataag    1380
gagtcttaat gaccatgatt acggattcac tggccgtcgt tttacaacgt cgtgactggg    1440
aaaaccctgg cgttacccaa cttaatcgcc ttgcagcaca tccccctttc gccagctggc    1500
gtaatagcga agaggcccgc accgatcgcc cttcccaaca gttgcgcagc ctgaatggcg    1560
aatggcgctt tgcctggttt ccggcaccag aagcggtgcc ggaaagctgg ctggagtgcg    1620
atcttcctga ggccgatact gtcgtcgtcc cctcaaactg gcagatgcac ggttacgatg    1680
```

```
cgcccatcta caccaacgtg acctatccca ttacggtcaa tccgccgttt gttcccacgg   1740
agaatccgac gggttgttac tcgctcacat ttaatgttga tgaaagctgg ctacaggaag   1800
gccagacgcg aattattttt gatggcgtta actcggcgta aaagaggag aaatactaga    1860 tgaccatgat tacggattca ctggccgtcg ttttacaacg tcgtgactgg gaaaaccctg   1920
gcgttaccca acttaatcgc cttgcagcac atcccccttt cgccagctgg cgtaatagcg   1980
aagaggcccg caccgatcgc ccttcccaac agttgcgcag cctgaatggc gaatggcgct   2040
ttgcctggtt tccggcacca gaagcggtgc cggaaagctg gctggagtgc gatcttcctg   2100
aggccgatac tgtcgtcgtc ccctcaaact ggcagatgca cggttacgat gcgcccatct   2160
acaccaacgt gacctatccc attacggtca atccgccgtt tgttcccacg gagaatccga   2220
cgggttgtta ctcgctcaca tttaatgttg atgaaagctg gctacaggaa ggccagacgc   2280
gaattatttt tgatggcgtt aactcggcgt aatattgctg tcctttgaac caatgaatga   2340
tttgatgagc caaaaaaatg taatcaatat tgttgatgat aatattaaga agtaccacac   2400
ggaatatacc taaacttaat taacggcact cctcagcaaa tataatgacc ctcttgataa   2460
cccaagaggg cattttttaa tgcccatggc gtttaccaat gcttaatcag tgaggcacct   2520
atctcagcga tctgtctatt tcgttcatcc atagttgcct gactccccgt cgtgtagata   2580
actacgatac gggagggctt accatctggc cccagtgctg caatgatacc gcgagaccca   2640
cgctcaccgg ctccagattt atcagcaata accagccag ccggaagggc cgagcgcaga    2700
agtggtcctg caactttatc cgcctccatc cagtctatta attgttgccg ggaagctaga   2760
gtaagtagtt cgccagttaa tagtttgcgc aacgttgttg ccattgctac aggcatcgtg   2820
gtgtcacgct cgtcgtttgg tatggcttca ttcagctccg gttcccaacg atcaaggcga   2880
gttacatgat cccccatgtt gtgcaaaaaa gcggttagct ccttcggtcc tccgatcgtt   2940
gtcagaagta agttggccgc agtgttatca ctcatggtta tggcagcact gcataattct   3000
cttactgtca tgccatccgt aagatgcttt tctgtgactg gtgagtactc aaccaagtca   3060
ttctgagaat agtgtatgcg gcgaccgagt tgctcttgcc cggcgtcaat acgggataat   3120
accgcgccac atagcagaac tttaaaagtg ctcatcattg gaaaacgttc ttcggggcga   3180
aaactctcaa ggatcttacc gctgttgaga tccagttcga tgtaacccac tcgtgcaccc   3240
aactgatctt cagcatcttt tactttcacc agcgtttctg ggtgagcaaa aacaggaagg   3300
caaaatgccg caaaaaaggg aataagggcg acacggaaat gttgaatact catactcttc   3360 cttttcaat attattgaag catttatcag ggttattgtc tcatgagcgg atacatattt    3420
gaatgtattt agaaaaataa acaaataggg gttccgcgca catttccccg aaaagtgcca   3480
cctgacgtct aagaaaccat tattatcatg acattaacct ataaaaatag gcgtatcacg   3540
aggcccttag gccaaatagg ccgttcagat ccttccgtat ttagccagta tgttctctag   3600
tgtggttcgt tgttttgcg tgagccatga gaacgaacca ttgagatcat gcttactttg    3660
catgtcactc aaaaattttg cctcaaaact ggtgagctga attttgcag ttaaagcatc    3720 gtgtagtgtt tttcttagtc cgttacgtag gtaggaatct gatgtaatgg ttgttggtat   3780
tttgtcacca ttcatttta tctggttgtt ctcaagttcg gttacgagat ccatttgtct   3840
atctagttca acttggaaaa tcaacgtatc agtcgggcgg cctcgcttat caaccaccaa   3900
tttcatattg ctgtaagtgt ttaaatcttt acttattggt ttcaaaaccc attggttaag   3960
ccttttaaac tcatggtagt tattttcaag cattaacatg aacttaaatt catcaaggct   4020
```

| aatctctata | tttgccttgt | gagttttctt | ttgtgttagt | tcttttaata | accactcata | 4080 |
| aatcctcata | gagtatttgt | tttcaaaaga | cttaacatgt | tccagattat | attttatgaa | 4140 |
| ttttttttaac | tggaaaagat | aaggcaatat | ctcttcacta | aaaactaatt | ctaatttttc | 4200 |
| gcttgagaac | ttggcatagt | ttgtccactg | gaaaatctca | aagcctttaa | ccaaaggatt | 4260 |
| cctgatttcc | acagttctcg | tcatcagctc | tctggttgct | ttagctaata | caccataagc | 4320 |
| attttcccta | ctgatgttca | tcatctgagc | gtattggtta | taagtgaacg | ataccgtccg | 4380 |
| ttctttcctt | gtagggtttt | caatcgtggg | gttgagtagt | gccacacagc | ataaaattag | 4440 |
| cttggtttca | tgctccgtta | agtcatagcg | actaatcgct | agttcatttg | ctttgaaaac | 4500 |
| aactaattca | gacatacatc | tcaattggtc | taggtgattt | taatcactat | accaattgag | 4560 |
| atgggctagt | caatgataat | tactagtcct | tttcctttga | gttgtgggta | tctgtaaatt | 4620 |
| ctgctagacc | tttgctggaa | aacttgtaaa | ttctgctaga | ccctctgtaa | attccgctag | 4680 |
| acctttgtgt | gttttttttg | tttatattca | agtggttata | atttatagaa | taaagaaaga | 4740 |
| ataaaaaaag | ataaaaagaa | tagatcccag | ccctgtgtat | aactcactac | tttagtcagt | 4800 |
| tccgcagtat | tacaaaagga | tgtcgcaaac | gctgtttgct | cctctacaaa | acagacctta | 4860 |
| aaaccctaaa | ggcttaagta | gcaccctcgc | aagctcgggc | aaatcgctga | atattcctt | 4920 |
| tgtctccgac | catcaggcac | ctgagtcgct | gtcttttcg | tgacattcag | ttcgctgcgc | 4980 |
| tcacggctct | ggcagtgaat | gggggtaaat | ggcactacag | gcgccttta | tggattcatg | 5040 |
| caaggaaact | acccataata | caagaaaagc | ccgtcacggg | cttctcaggg | cgttttatgg | 5100 |
| cgggtctgct | atgtggtgct | atctgacttt | ttgctgttca | gcagttcctg | ccctctgatt | 5160 |
| ttccagtctg | accacttcgg | attatcccgt | gacaggtcat | tcagactggc | taatgcaccc | 5220 |
| agtaaggcag | cggtatcatc | aacaggctta | cccgtcttac | tgtcaagagg | acatccggtc | 5280 |
| aaataaaacg | aaaggctcag | tcgaaagact | gggcctttcg | | | 5320 |

<210> SEQ ID NO 5
<211> LENGTH: 4849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| ttttgctgag | gagacttagg | gaccctacat | aatacgactc | actatagggg | aaagacctgc | 60 |
| aggtgcagta | aggaggaaaa | aaaaatgaaa | aaattattat | tcgcaattcc | tttagttgtt | 120 |
| cctttctatt | ctcactccgc | tgaaactgtt | catcaccatc | accatcacgc | tgaaactgtt | 180 |
| gaaagttgtt | tagcaaaacc | ccatacagaa | aattcattta | ctaacgtctg | gaaagacgac | 240 |
| aaaactttag | atcgttacgc | taactatgag | ggctgtctgt | ggaatgctac | aggcgttgta | 300 |
| gtttgtactg | gtgacgaaac | tcagtgttac | ggtacatggg | ttcctattgg | gcttgctatc | 360 |
| cctgaaaatg | agggtggtgg | ctctgagggt | ggcggttctg | agggtggcgg | ttctgagggt | 420 |
| ggcggtacta | aacctcctga | gtacggtgat | acacctattc | cgggctatac | ttatatcaac | 480 |
| cctctcgacg | gcacttatcc | gcctggtact | gagcaaaacc | ccgctaatcc | taatccttct | 540 |
| cttgaggagt | ctcagcctct | taatactttc | atgtttcaga | ataataggtt | ccgaaatagg | 600 |
| cagggggcat | taactgttta | tacgggcact | gttactcaag | gcactgaccc | cgttaaaact | 660 |
| tattaccagt | acactcctgt | atcatcaaaa | gccatgtatg | acgcttactg | gaacggtaaa | 720 |

```
ttcagagact gcgctttcca ttctggcttt aatgaggatc cattcgtttg tgaatatcaa    780
ggccaatcgt ctgacctgcc tcaacctcct gtcaatgctg gcggcggctc tggtggtggt    840
tctggtggcg gctctgaggg tggtggctct gagggtggcg gttctgaggg tggcggctct    900
gagggaggcg gttccggtgg tggctctggt tccggtgatt ttgattatga aaagatggca    960
aacgctaata agggggctat gaccgaaaat gccgatgaaa acgcgctaca gtctgacgct   1020
aaaggcaaac ttgattctgt cgctactgat tacggtgctg ctatcgatgg tttcattggt   1080
gacgtttccg gccttgctaa tggtaatggt gctactggtg attttgctgg ctctaattcc   1140
caaatggctc aagtcggtga cggtgataat tcacctttaa tgaataattt ccgtcaatat   1200
ttaccttccc tccctcaatc ggttgaatgt cgcccttttg tctttggcgc tggtaaacct   1260
tacgagttca gtatcgactg cgataagatc aacctgttcc gcggtgtctt tgcgtttctt   1320
ttatatgttg ccacctttat gtatgtattt tctacgtttg ctaacatact gcgtaataag   1380
gagtcttaat gaccatgatt acggattcac tggccgtcgt tttacaacgt cgtgactggg   1440
aaaaccctgg cgttacccaa cttaatcgcc ttgcagcaca tccccctttc gccagctggc   1500
gtaatagcga agaggcccgc accgatcgcc cttcccaaca gttgcgcagc ctgaatggcg   1560
aatggcgctt tgcctggttt ccggcaccag aagcggtgcc ggaaagctgg ctggagtgcg   1620
atcttcctga ggccgatact gtcgtcgtcc cctcaaactg gcagatgcac ggttacgatg   1680
cgcccatcta caccaacgtg acctatccca ttacggtcaa tccgccgttt gttcccacgg   1740
agaatccgac gggttgttac tcgctcacat ttaatgttga tgaaagctgg ctacaggaag   1800
gccagacgcg aattattttt gatggcgtta actcggcgta atattgctgt cctttgaacc   1860
aatgaatgat ttgatgagcc aaaaaaatgt aatcaatatt gttgatgata atattaagaa   1920
gtaccacacg gaatatacct aaacttaatt aacggcactc ctcagcaaat ataatgaccc   1980
tcttgataac ccaagagggc atttttttaat gcccatggcg tttaccaatg cttaatcagt   2040
gaggcaccta tctcagcgat ctgtctattt cgttcatcca tagttgcctg actccccgtc   2100
gtgtagataa ctacgatacg ggagggctta ccatctggcc ccagtgctgc aatgataccg   2160
cgagacccac gctcaccggc tccagattta tcagcaataa accagccagc cggaagggcc   2220
gagcgcagaa gtggtcctgc aactttatcc gcctccatcc agtctattaa ttgttgccgg   2280
gaagctagag taagtagttc gccagttaat agtttgcgca acgttgttgc cattgctaca   2340
ggcatcgtgg tgtcacgctc gtcgtttggt atggcttcat tcagctccgg ttcccaacga   2400
tcaaggcgag ttacatgatc ccccatgttg tgcaaaaaag cggttagctc cttcggtcct   2460
ccgatcgttg tcagaagtaa gttggccgca gtgttatcac tcatggttat ggcagcactg   2520
cataattctc ttactgtcat gccatccgta agatgctttt ctgtgactgg tgagtactca   2580
accaagtcat tctgagaata gtgtatgcgg cgaccgagtt gctcttgccc ggcgtcaata   2640
cgggataata ccgcgccaca tagcagaact ttaaaagtgc tcatcattgg aaaacgttct   2700
tcggggcgaa aactctcaag gatcttaccg ctgttgagat ccagttcgat gtaacccact   2760
cgtgcaccca actgatcttc agcatctttt actttcacca gcgtttctgg gtgagcaaaa   2820
acaggaaggc aaaatgccgc aaaaaaggga ataagggcga cacggaaatg ttgaatactc   2880
atactcttcc tttttcaata ttattgaagc atttatcagg gttattgtct catgagcgga   2940
tacatatttg aatgtattta gaaaaataaa caaataggg ttccgcgcac atttccccga   3000
aaagtgccac ctgacgtcta agaaaccatt attatcatga cattaaccta taaaaatagg   3060
cgtatcacga ggcccttagg ccaaataggc cgttcagatc cttccgtatt tagccagtat   3120
```

```
gttctctagt gtggttcgtt gtttttgcgt gagccatgag aacgaaccat tgagatcatg    3180
cttactttgc atgtcactca aaattttgc ctcaaaactg gtgagctgaa tttttgcagt    3240
taaagcatcg tgtagtgttt ttcttagtcc gttacgtagg taggaatctg atgtaatggt    3300
tgttggtatt ttgtcaccat tcattttat ctggttgttc tcaagttcgg ttacgagatc    3360
catttgtcta tctagttcaa cttggaaaat caacgtatca gtcgggcggc ctcgcttatc    3420
aaccaccaat ttcatattgc tgtaagtgtt taaatcttta cttattggtt tcaaaaccca    3480
ttggttaagc cttttaaact catggtagtt attttcaagc attaacatga acttaaattc    3540
atcaaggcta atctctatat ttgccttgtg agttttcttt tgtgttagtt cttttaataa    3600
ccactcataa atcctcatag agtatttgtt ttcaaaagac ttaacatgtt ccagattata    3660
ttttatgaat ttttttaact ggaaaagata aggcaatatc tcttcactaa aaactaattc    3720
taatttttcg cttgagaact tggcatagtt tgtccactgg aaaatctcaa agcctttaac    3780
caaaggattc ctgatttcca cagttctcgt catcagctct ctggttgctt tagctaatac    3840
accataagca ttttccctac tgatgttcat catctgagcg tattggttat aagtgaacga    3900
taccgtccgt tctttccttg tagggttttc aatcgtgggg ttgagtagtg ccacacagca    3960
taaaattagc ttggtttcat gctccgttaa gtcatagcga ctaatcgcta gttcatttgc    4020
tttgaaaaca actaattcag acatacatct caattggtct aggtgatttt aatcactata    4080
ccaattgaga tgggctagtc aatgataatt actagtcctt ttcctttgag ttgtgggtat    4140
ctgtaaattc tgctagacct ttgctggaaa acttgtaaat tctgctagac cctctgtaaa    4200
ttccgctaga cctttgtgtg ttttttttgt ttatattcaa gtggttataa tttatagaat    4260
aaagaaagaa taaaaaaga taaaagaat agatcccagc cctgtgtata actcactact    4320
ttagtcagtt ccgcagtatt acaaaggat gtcgcaaacg ctgtttgctc ctctacaaaa    4380
cagaccttaa aaccctaaag gcttaagtag caccctcgca agctcgggca aatcgctgaa    4440
tattcctttt gtctccgacc atcaggcacc tgagtcgctg tcttttcgt gacattcagt    4500 tcgctgcgct cacggctctg gcagtgaatg ggggtaaatg gcactacagg cgccttttat    4560
ggattcatgc aaggaaacta cccataatac aagaaaagcc cgtcacgggc ttctcagggc    4620
gttttatggc gggtctgcta tgtggtgcta tctgactttt tgctgttcag cagttcctgc    4680
cctctgattt tccagtctga ccacttcgga ttatcccgtg acaggtcatt cagactggct    4740
aatgcaccca gtaaggcagc ggtatcatca acaggcttac ccgtcttact gtcaagagga    4800
catccggtca aataaaacga aaggctcagt cgaaagactg ggcctttcg                4849
```

```
<210> SEQ ID NO 6
<211> LENGTH: 3601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ttgagatcct ttttttctgc gcttttttcca taggctccgc cccctgaca agcatcacga      60 aatctgacgc tcaaatcagt ggtggcgaaa cccgacagga ctataaagat accaggcgtt    120
tccccctggc ggctccctcg tgcgctctcc tgttcctgcc tttcggttta ccggtgtcat    180
tccgctgtta tggccgcgtt tgtctcattc cacgcctgac actcagttcc gggtaggcag    240
ttcgctccaa gctggactgt atgcacgaac ccccgttca gtccgaccgc tgcgccttat    300
```

```
ccggtaacta tcgtcttgag tccagcccgg aaagacatgc aaagcaccca ctggcagcag      360
ccactggtaa ttgatttaga ggagttagtc ttgaagtcat gcgccggtta aggctaaact      420
gaaaggacaa gttttggtga ctgcgctcct ccaagccagt tacctcggtt caaagagctg      480
gtagctcaga gaaccttcga aaaccgccc tgcaaggcgg ttttttcgtt ttcagagcaa       540
gagattacgc gcagaccaaa acgatctcaa gaagatcatc ttattaatcc tctgccagtg      600
ttacaaccac acgatacggg ttactgatga tgaacaagag gacatccggt caaataaaac     660
gaaaggctca gtcgaaagac tgggcctttc gttttgctga ggagacttag ggaccctact     720
aatacgactc actataggga gaaaggctaa taggtaccgg tgataccagc atcgtcttga     780
tgcccttggc agcaccctgc taaggtaaca acaagatgaa aaaattatta ttcgcaattc     840
ctttagtggt gccttctat tctcactccg ctgaaactgt tcatcaccat caccatcacg      900
ctgaaactgt tgaaagttgt ttagcaaaac cccatacaga aaattcattt actaacgtct     960
ggaaagacga caaaacttta gatcgttacg ctaactatga gggctgtctg tggaatgcta     1020
caggcgttgt agtttgtact ggtgacgaaa ctcagtgtta cggtacatgg gttcctattg     1080
ggcttgctat ccctgaaaat gagggtggtg gctctgaggg tggcggttct gagggtggcg     1140
gttctgaggg tggcggtact aaacctcctg agtacggtga tacacctatt ccgggctata    1200
cttatatcaa ccctctcgac ggcacttatc cgcctggtac tgagcaaaac cccgctaatc     1260
ctaatccttc tcttgaggag tctcagcctc ttaatacttt catgtttcag aataataggt     1320
tccgaaatag gcaggggca ttaactgttt atacgggcac tgttactcaa ggcactgacc      1380
ccgttaaaac ttattaccag tacactcctg tatcatcaaa agccatgtat gacgcttact     1440
ggaacggtaa attcagagac tgcgctttcc attctggctt taatgaggat ccattcgttt     1500
gtgaatatca aggccaatcg tctgacctgc ctcaacctcc tgtcaatgct ggcggcggct     1560
ctggtggtgg ttctggtggc ggctctgagg gtggtggctc tgagggtggc ggttctgagg     1620
gtggcggctc tgagggaggc ggttccggtg gtggctcttc ccaaatggct caagtcggtg     1680
acggtgataa ttcaccttta atgaataatt tccgtcaata tttaccttcc ctccctcaat    1740
cggttgaatg tcgcccttt gtctttggcg ctggtaaacc ttacgagttc agtatcgact      1800
gcgataagat caacctgttc cgcggtgtct ttgcgtttct tttatatgtt gccaccttta     1860
tgtatgtatt ttctacgttt gctaacatac tgcgtaataa ggagtcttaa tggtcagtaa     1920
aggagaagaa cttttcactg gagttgtccc aattcttgtt gaattagatg gtgatgttaa     1980
tgggcacaaa ttttctgtca gtggagaggg tgaaggtgat gcaacatacg gaaaacttac     2040
ccttaaactg atttgcacta ctggaaaact acctgttcca tggccaacac ttgtcactac     2100
tctgggctat ggtctgcaat gctttgccag atacccagat catatgaaac agcatgactt     2160
tttcaagagt gccatgcccg aaggttatgt acaggaaaga actatatttt tcaaagatga     2220
cgggaactac aagacacgtg ctgaagtcaa gtttgaaggt gatacccttg ttaatagaat     2280
cgagttaaaa ggtattgatt ttaaagaaga tggaaacatt cttggacaca aattggaata     2340
caactataac tcacacaatg tatacatcac cgcagacaaa caaaagaatg gaatcaaagc     2400
caacttcaaa attagacaca acattgaaga tggaggcgtt caactagcag accattatca     2460
acaaaatact ccaattggcg atggccctgt ccttttacca gacaaccatt acctgtccta     2520
ccaatctgcc ctttcgaaag atcccaacga aaagagagac cacatggtcc ttcttgagtt     2580
tgtaacagct gctgggatta cacatggcat ggatgaacta tacaaataaa cttaattaac     2640
```

```
ggcactcctc agcaaatata atgaccctct tgataaccca agagggcatt ttttaatgcc      2700
catggcgttt atttgccgac taccttggtg atctcgcctt tcacgtagtg gacaaattct      2760
tccaactgat ctgcgcgcga ggccaagcga tcttcttctt gtccaagata agcctgtcta      2820
gcttcaagta tgacgggctg atactgggcc ggcaggcgct ccattgccca gtcggcagcg      2880
acatccttcg gcgcgatttt gccggttact gcgctgtacc aaatgcggga caacgtaagc      2940
actacatttc gctcatcgcc agcccagtcg ggcggcgagt tccatagcgt taaggtttca      3000
tttagcgcct caaatagatc ctgttcagga accggatcaa agagttcctc cgccgctgga      3060
cctaccaagg caacgctatg ttctcttgct tttgtcagca agatagccag atcaatgtcg      3120
atcgtggctg gctcgaagat acctgcaaga atgtcattgc gctgccattc tccaaattgc      3180
agttcgcgct tagctggata acgccacgga atgatgtcgt cgtgcacaac aatggtgact      3240
tctacagcgc ggagaatctc gctctctcca ggggaagccg aagtttccaa aaggtcgttg      3300
atcaaagctc gccgcgttgt tcatcaagc cttacggtca ccgtaaccag caaatcaata      3360
tcactgtgtg gcttcaggcc gccatccact gcggagccgt acaaatgtac ggccagcaac      3420
gtcggttcga gatggcgctc gatgacgcca actacctctg atagttgagt cgatacttcg      3480
gcgatcaccg cttccctcat actcttcctt tttcaatatt attgaagcat ttatcagggt      3540
tattgtctca tgagcggata catatttgaa tgtatttaga aaaataggcc aaataggccg      3600
t                                                                     3601
```

<210> SEQ ID NO 7
<211> LENGTH: 4021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
cactcggtcg ctacgctccg ggcgtgagac tgcggcgggc gctgcggaca catacaaagt       60
tacccacaga ttccgtggat aagcaggga ctaacatgtg aggcaaaaca gcagggccgc      120
gccggtggcg tttttccata ggctccgccc tcctgccaga gttcacataa acagacgctt      180
ttccggtgca tctgtgggag ccgtgaggct caaccatgaa tctgacagta cgggcgaaac      240
ccgacaggac ttaaagatcc ccaccgtttc cggcgggtcg ctccctcttg cgctctcctg      300
ttccgaccct gccgtttacc ggatacctgt tccgcctttc tcccttacgg gaagtgtggc      360
gctttctcat agctcacaca ctggtatctc ggctcggtgt aggtcgttcg ctccaagctg      420
ggctgtaagc aagaactccc cgttcagccc gactgctgcg ccttatccgg taactgttca      480
cttgagtcca acccggaaaa gcacggtaaa acgccactgg cagcagccat ggtaactgg       540 gagttcgcag aggatttgtt tagctaaaca cgcggttgct cttgaagtgt gcgccaaagt      600
ccggctacac tggaaggaca gatttggttg ctgtgctctg cgaaagccag ttaccacggt      660
taagcagttc cccaactgac ttaaccttcg atcaaaccac ctccccaggt ggttttttcg      720
tttacagggc aaaagattac gcgcagaaaa aaggatctc aagaagatcc tttgatcttt      780
tctactgaac cgctctagat ttcagtgcaa tttatctctt caaatgtagc acctgaagtc      840 agccccaggag gaagaggaca tccggtcaaa taaaacgaaa ggctcagtcg aaagactggg      900
cctttcgttt tagacttagg gaccctttat gacaacttga cggctacaat taaccctcac      960
taaagggaga aagacctgca ggtgcagtaa ggaggaaaaa aaaatgagca ctgcaattac     1020
```

-continued

```
acgccagatc gttctcgcta ccgcaaccac cggtatgaac cagattggtg cgcactatga    1080
aggccacaag atcattgaga ttggtgccgt tgaagtggtg aaccgtcgcc tgacgggcaa    1140
taacttccat gtttatctca aacccgatcg gctggtggat ccggaagcct tggcgtaca     1200 tggtattgcc gatgaatttt tgctcgataa gcccacgttt gccgaagtag ccgatgagtt    1260
catggactat attcgcggcg cggagttggt gatccataac gcagcgttcg atatcggctt    1320
tatggactac gagttttcgt tgcttaagcg cgatattccg aagaccaata ctttctgtaa    1380
ggtcaccgat agccttgcgg tggcgaggaa aatgtttccc ggtaagcgca acagcctcga    1440
tgcgttatgt gctcgctacg aaatagataa cagtaaacga acgctgcacg ggcattact     1500 cgatgcccag atccttgcgg aagtttatct ggcgatgacc ggtggtcaaa cgtcgatggc    1560
ttttgcgatg gaaggagaga cacaacagca acaaggtgaa gcaacaattc agcgcattgt    1620
acgtcaggca agtaagttac gcgttgtttt tgcgacagat gaagagattg cagctcatga    1680
agcccgtctc gatctggtgc agaagaaagg cggaagttgc ctctggcgag cataatttaa    1740
tatcagtaaa ccggacataa cccatgaaga aaaatcgcgc ttttttgaag tgggcagggg    1800
gcaagtatcc cctgcttgat gatattaaac ggcatttgcc caagggcgaa tgtctggttg    1860
agccttttgt aggtgccggg tcggtgtttc tcaacaccga cttttctcgt tatatccttg    1920
ccgatatcaa tagcgacctg atcagtctct ataacattgt gaagatgcgt actgatgagt    1980
acgtacaggc cgcacgcgag ctgtttgttc ccgaaacaaa ttgcgccgag gtttactatc    2040
agttccgcga agagttcaac aaaagccagg atccgttccg tcgggcggta ctgttttat     2100 atttgaaccg ctacgttac aacggcctgt gtcgttacaa tctgcgcggt gagttttaacg    2160 tgccgttcgg ccgctacaaa aaaccctatt tcccggaagc agagttgtat cacttcgctg    2220
aaaaagcgca gaatgccttt ttctattgtg agtcttacgc cgatagcatg gcgcgcgcag    2280
atgatgcatc cgtcgtctat tgcgatccgc cttatgcacc gctgtctgcg accgccaact    2340
ttacggcgta tcacacaaac agttttacgc ttgaacaaca agcgcatctg gcggagatcg    2400
ccgaaggtct ggttgagcgc catattccag tgctgatctc caatcacgat acgatgttaa    2460
cgcgtgagtg gtatcagcgc gcaaaattgc atgtcgtcaa agttcgacgc agtataagca    2520
gcaacggcgg cacacgtaaa aaggtggacg aactgctggc tttgtacaaa ccaggagtcg    2580
tttcacccgc gaaaaaataa ttcagctaag acactgcact ggattaagat gaaaacgatt    2640
gaagttgatg atgaactcta cagctatatt gccagccaca ctaagcatat cggcgagagc    2700
gcatccgaca ttttacggcg tatgttgaaa ttttccgccg catcacagcc tgctgctccg    2760
gtgacgaaag aggttcgcgt tgcgtcacct gctatcgtcg aagcgaagcc ggtcaaaacg    2820
attaaagaca aggttcgcgc aatgcgtgaa cttctgcttt cggatgaata cgcagagcaa    2880
aagcgagcgg tcaatcgctt tatgctgctg ttgtctacac tatattctct tgacgcccag    2940
gcgtttgccg aagcaacgga atcgttgcac ggtcgtacac gcgtttactt tgcggcagat    3000
gaacaaacgc tgctgaaaaa tggtaatcag accaagccga acatgtgcc aggcacgccg     3060 tattgggtga tcaccaacac caacaccggc cgtaaatgca gcatgatcga acacatcatg    3120
cagtcgatgc aattcccggc ggaattgatt gagaaggttt gcggaactat ctaaacttaa    3180
ttaacggcac tcctcagcca agtcaaaagc ctccgaccgg aggcttttga ctacatgccc    3240
atggcgttta cgccccgccc tgccactcat cgcagtactg ttgtaattca ttaagcattc    3300
tgccgacatg gaagccatca caaacggcat gatgaacctg aatcgccagc ggcatcagca    3360
ccttgtcgcc ttgcgtataa tatttgccca tagtgaaaac gggggcgaag aagttgtcca    3420
```

```
tattggccac gtttaaatca aaactggtga aactcaccca gggattggct gagacgaaaa    3480
acatattctc aataaaccct ttagggaaat aggccaggtt ttcaccgtaa cacgccacat    3540
cttgcgaata tatgtgtaga aactgccgga aatcgtcgtg gtattcactc cagagcgatg    3600
aaaacgtttc agtttgctca tggaaaacgg tgtaacaagg gtgaacacta tcccatatca    3660
ccagctcacc gtctttcatt gccatacgga actccggatg agcattcatc aggcgggcaa    3720
gaatgtgaat aaaggccgga taaaacttgt gcttattttt ctttacggtc tttaaaaagg    3780
ccgtaatatc cagctgaacg gtctggttat aggtacattg agtaactgac tgaaatgcct    3840
caaaatgttc tttacgatgc cattgggata tatcaacggt ggtatatcca gtgatttttt    3900
tctccatttt agcttcctta gctcctgaaa atctcgataa ctcaaaaaat acgcccggta    3960
gtgatcttat ttcattatgg tgaaagttgg aacctcttac gtgccaagcc aaataggccg    4020
t                                                                    4021
```